(12) United States Patent
Gormley et al.

(10) Patent No.: US 9,376,678 B2
(45) Date of Patent: Jun. 28, 2016

(54) METHOD OF PREPARING LIBRARIES OF TEMPLATE POLYNUCLEOTIDES

(71) Applicant: ILLUMINA CAMBRIDGE LIMITED, Nr. Saffron Walden (GB)

(72) Inventors: Niall Anthony Gormley, Nr. Saffron Walden (GB); Geoffrey Paul Smith, Nr Saffron Walden (GB); David Bentley, Nr Saffron Walden (GB); Roberto Rigatti, Nr Saffron Walden (GB); Shujun Luo, Hayward, CA (US)

(73) Assignee: Illumina Cambridge Limited, Nr Saffron Walden (GB)

( * ) Notice: Subject to any disclaimer, the term of this patent is extended or adjusted under 35 U.S.C. 154(b) by 456 days.

(21) Appl. No.: 14/022,470

(22) Filed: Sep. 10, 2013

(65) Prior Publication Data

US 2014/0066335 A1    Mar. 6, 2014

Related U.S. Application Data

(63) Continuation of application No. 12/799,172, filed on Apr. 20, 2010, now Pat. No. 8,563,478, which is a continuation of application No. 11/486,953, filed on Jul. 14, 2006, now Pat. No. 7,741,763.

(30) Foreign Application Priority Data

Nov. 1, 2005 (GB) .................................... 522310.2

(51) Int. Cl.
   *C40B 40/06* (2006.01)
   *C12N 15/10* (2006.01)
   *C12Q 1/68* (2006.01)

(52) U.S. Cl.
   CPC .......... *C12N 15/1096* (2013.01); *C12Q 1/6855* (2013.01); *C40B 40/06* (2013.01); *Y10T 436/143333* (2015.01)

(58) Field of Classification Search
   None
   See application file for complete search history.

(56) References Cited

U.S. PATENT DOCUMENTS

| | | |
|---|---|---|
| 4,719,179 A | 1/1988 | Barany |
| 5,093,245 A | 3/1992 | Keith et al. |
| 5,326,692 A | 7/1994 | Brinkley et al. |
| 5,436,142 A | 7/1995 | Wigler et al. |
| 5,508,169 A | 4/1996 | Deugau et al. |

(Continued)

FOREIGN PATENT DOCUMENTS

| | | |
|---|---|---|
| EP | 0 224 126 | 6/1987 |
| EP | 0 201 184 | 12/1992 |

(Continued)

OTHER PUBLICATIONS

Adessi, et al., "Solid Phase DNA amplification: characterisation of primer attachment and amplification mechanisms", Nucleic Acids Research 28, 2000, 1-8.

(Continued)

*Primary Examiner* — Christian Boesen
(74) *Attorney, Agent, or Firm* — Brent C. Moore; Illumina, Inc.

(57) ABSTRACT

The present invention relates to a method for preparing a library of template polynucleotides and use thereof in methods of solid-phase nucleic acid amplification. More specifically, the invention relates to a method for preparing a library of template polynucleotides that have common sequences at their 5' ends and at their 3' ends.

4 Claims, 12 Drawing Sheets

(56) References Cited

U.S. PATENT DOCUMENTS

| | | | |
|---|---|---|---|
| 5,514,539 | A | 5/1996 | Bukh et al. |
| 5,589,332 | A | 12/1996 | Shih et al. |
| 5,616,478 | A | 4/1997 | Chetverin |
| 5,641,658 | A | 6/1997 | Adams et al. |
| 5,645,994 | A | 7/1997 | Huang |
| 5,750,337 | A | 5/1998 | Squirrell et al. |
| 5,753,439 | A | 5/1998 | Smith et al. |
| 5,759,822 | A | 6/1998 | Chenchik et al. |
| 5,800,992 | A | 9/1998 | Fodor et al. |
| 5,837,466 | A | 11/1998 | Lane et al. |
| 5,843,660 | A | 12/1998 | Schumm et al. |
| 5,939,291 | A | 8/1999 | Loewy et al. |
| 5,942,391 | A | 8/1999 | Zhang et al. |
| 6,033,881 | A | 3/2000 | Himmler et al. |
| 6,045,994 | A | 4/2000 | Zabeau et al. |
| 6,054,276 | A | 4/2000 | Macevicz |
| 6,060,288 | A | 5/2000 | Adams et al. |
| 6,090,592 | A | 7/2000 | Adams et al. |
| 6,107,023 | A | 8/2000 | Reyes et al. |
| 6,114,149 | A | 9/2000 | Fry et al. |
| 6,150,112 | A | 11/2000 | Weissman et al. |
| 6,261,770 | B1 | 7/2001 | Warthoe |
| 6,277,606 | B1 | 8/2001 | Wigler et al. |
| 6,287,825 | B1 | 9/2001 | Weissman et al. |
| 6,361,947 | B1 | 3/2002 | Dong et al. |
| 6,372,434 | B1 | 4/2002 | Weissman et al. |
| 6,395,887 | B1 | 5/2002 | Weissman et al. |
| 6,406,893 | B1 | 6/2002 | Knapp et al. |
| 7,115,400 | B1 | 10/2006 | Adessi et al. |
| 2004/0067493 | A1 | 4/2004 | Matsuzaki et al. |
| 2004/0137473 | A1 | 7/2004 | Wigler et al. |
| 2005/0095645 | A1 | 5/2005 | Jones et al. |
| 2005/0100900 | A1 | 5/2005 | Kawashima et al. |
| 2009/0176662 | A1 | 7/2009 | Rigatti et al. |

FOREIGN PATENT DOCUMENTS

| | | |
|---|---|---|
| EP | 0543484 | 5/1993 |
| EP | 0 356 025 B1 | 4/1994 |
| EP | 0 665 293 | 8/1995 |
| GB | 2412170 | 9/2005 |
| WO | 87/06270 | 10/1987 |
| WO | 89/12695 | 12/1989 |
| WO | 91/06678 | 5/1991 |
| WO | 93/04199 | 3/1993 |
| WO | 94/02634 | 2/1994 |
| WO | 94/03624 | 2/1994 |
| WO | 95/33073 | 12/1995 |
| WO | 96/04404 | 2/1996 |
| WO | 96/32504 | 10/1996 |
| WO | 97/04126 | 2/1997 |
| WO | 97/47767 | 12/1997 |
| WO | 98/36094 | 8/1998 |
| WO | 98/44151 | 10/1998 |
| WO | 98/44152 | 10/1998 |
| WO | 98/45474 | 10/1998 |
| WO | 00/18957 | 4/2000 |
| WO | 00/23620 | 4/2000 |
| WO | 00/41524 | 7/2000 |
| WO | 00/47767 | 8/2000 |
| WO | 2004/053163 | 3/2004 |
| WO | 2004/070007 | 8/2004 |
| WO | 2004/081183 | 9/2004 |
| WO | 2005/090599 | 9/2005 |

OTHER PUBLICATIONS

Chang, et al., "PCR Amplification of Chromosome-specific DNA Isolated from Flow Cytometry-Sorted Chromosomes", Genomics 12, 1992, 307-312.

Chenchik, et al., "Full length cDNA cloning", BioTechniques vol. 21, 1996, 526-534.

Cheng, et al., "Chip PCR II Investigation of different PCR amplification systems in microfabricated silicon-glass chips", Nucleic Acids Research 24, 1996, 380-385.

Dressman, , "Supplmentary Table to Transforming single DNA molecules into fluorescent magnetic particles for detection and enumeration of genetic variations", PNAS 100, 2003, 8817-8822.

Dressman, et al., "Transforming single DNA molecules into fluorescent magnetic particles for detection and enumeration of genetic variations", PNAS, 100(15), 2003, 8817-8822.

Dubiley, et al., "Polymorphism analysis and gene detection by minisequencing on an array of gel-immobilized primers", Nucleic Acids Research 27, 1999, 1-6.

Ferguson, J A. et al., "A Fiber-Optic DNA Biosensor Microarray for the Analysis of Gene Expression", Nature Biotechnol. vol. 14, 1996, 1681-1684.

Fu, et al., "Sequencing Double-stranded DNA by Strand Displacement", Nucleic Acids Research vol. 25 No. 3, 1997, 677-679.

Gubler, et al., "A simple and very efficient method for generating cDNA Libraries", Gene 25, 1983, 263-269.

Hahn, et al., "Quantitative polymerase chain reaction with enzyme-linked immunosorbent assay detection of selectively digested amplified sample and control DNA", Anal Biochem 229, 1995, 236-248.

Helfman, et al., "Identification of clones that encode chicken tropomyosin by direct immunological screening of a cDNA expression library", PNAS US 80, 1983, 31-35.

Johnson, "Molecular Cloning of DNA from specific chromosomal regions by Microdissection and Sequence-Independent Amplification of DNA", Genomics 6, 1990, 243-251.

Kalisch, et al., "Covalently linked sequencing primer linkers (splinkers) for sequence analysis of restriction fragments", Gene 44, 1986, 263-270.

Kimmel, et al., "Preparation of cDNA and the Generation of cDNA Libraries: Overview", Methods in Enzymology 152, 1987, 307-316.

Kinzler, et al., "Whole genome PCR: application to the identification of sequences bound by gene regulatory proteins", Nucleic Acids Research, 17(10), 1989, 3645-3653.

Lizardi, , "Mutation detection and single-molecule counting using isothermal rolling-circle amplification", Nature Genetics, vol. 19, 1998, 225-232.

Lockhart, D J. et al., "Expression monitoring by hybridization to high-density oligonucleotide arrays", Nature Biotechnology, vol. 14 December, ISSN 1087-015., 1996, 1675-1680.

Lucito, et al., "Genetic analysis using genomic representations", PNAS, 95, 1998, 4487-4492.

Matsunaga, et al., "Selecting and amplifying one fragement from a DNA fragment mixture by polyermerase chain reaction with a pair of selective primers", Electrophoresis, vol. 17, 1996, 1833-1840.

Matsuzaki, "Parallel Genotyping of Over 10,000 SNPs Using a One-Primer Assay on a High-Density Oligonucleotide Array", Genome Research, 14, 2004, 414-425.

Mueller, et al., "In Vivo Footprinting of a muscle specific Enhancer by Ligation Mediated PCR", Science 246, 1989, 780-786.

Notomi, et al., "Loop-mediated isothermal amplification of DNA", Nucleic Acids Research 28, 2000, i-vii.

Nussbaum, et al., "Isolation of anonymous DNA Sequences from within a submicroscopic X chromosomal deletion in a patient with choroideremia, deafness and mental retardation", PNAS US 84, 1987, 6521-6525.

Ochman, et al., "Genetic applications of an Inverse Polymerase Chain Reaction", Genetics 120, 1988, 621-623.

Oliphant, et al., "Cloning of random-sequence oligodeoxynucleotides", Gene 44, 1986, 177-183.

Oroskar, et al., "Detection of immobilized amplicons by ELISA-like techniques", Clinical Chemistry 42, 1996, 1547-1555.

Pease, et al., "Light-generated oligonucleotide array for rapid DNA sequence analysis", Proc. Natl. Acad. Sci., vol. 91, Issue 11, 1994, 5502-5026.

Pfeifer, et al., "Genomic Sequencing and Methylation Analysis by Ligation Mediated PCR", Science 246, 1989, 810-813.

Saiki, et al., "Analysis of enzymatically amplified . . . -globin and HLA-DQ . . . DNA with allele-specific oligonucleotide probes", Nature 324, 1986, 163-166.

Saiki, et al., "Primer-Directed Enzymatic Amplification of DNA with a Thermostable DNA Polymerase", Science 239, 1988, 487-491.

Sanger, et al., "Cloning in Single-Stranded Bacteriophage as an Aid to Rapid DNA Sequencing", Mol Biologiy 143, 1980, 161-178.

(56) References Cited

OTHER PUBLICATIONS

Saunders, et al., "PCR amplification of DNA microdissected from a single polytene chromosome band: a comparison with conventional microcloning", Nucleic Acids Research 17, 1989, 9027-9037.

Steigerwald, et al., "Ligation-mediated PCR Improves the sensitivity of methylation analysis by restriction enzymes and detection of specific DNA Strand breaks", Nucleic Acids Research 18, 1990, 1435-1439.

Sterky, et al., "Direct sequencing of bacterial artificial chromosomes [bacS] prokaryotic genomes by biotin capture PCR", Journal of Biotechnology, vol. 60, 1998, 119-129.

Strick, et al., "Stress-Induced Structural Transistions of DNA and Proteins", Annu Rev. Biophys. Biomol. Struct. 29, 2000, 523-543.

Triglia, et al., "A procedure for in vitro amplification of DNA segments that lie outside the boundaries of know sequences", Nucleic Acids Research 16, 1988, 8186.

Velculescu, et al., "Serial analysis of gene expression", Science, 270, 1995, 484-487.

Walker, , "Empirical Aspects of Strand Displacement Amplification", PCR Methods Appl 3, 1993, 1-6.

Walker, et al., "Multiplex strand displacement amplification (SDA) and detection of DNA sequences from *Mycobacterium tuberculosis* and other mycobacteria", Nucleic Acids Research 22, 1994, 2670-2677.

Walker, et al., "Strand displacement amplification—an isothermal, in vitro DNA amplification technique", NAR, 20, 1992, 1691-1696.

Walter, et al., "Strand displacement amplification as an in vitro model for roling-circle replication: deletion formation and evolution during serial transfer", PNAS 91, 1994, 7937-7941.

Westin, et al., "Anchored multiplex amplification on a microelectric chip array", Nature Biotechnology 18, 2000, 199-204.

Yershov, et al., "DNA analysis and diagnostics on oligonucleotide microchips", PNAS US 93, 1996, 4913-4918.

Brownie, et al., "The elimination of primer-dimer accumulation in PCR", Nucleic Acids Research, vol. 25, No. 16, 1997, 3235-3241.

Notice of Opposition, "Application No. 06794950.3, mailed Oct. 16, 2014".

Prashar, et al., "Analysis of differential gene expression by display of 3' end restriction fragments of cDNAs", Department of Genetics, Boyer Center for Molecular Medicine, Oct. 5, 1995.

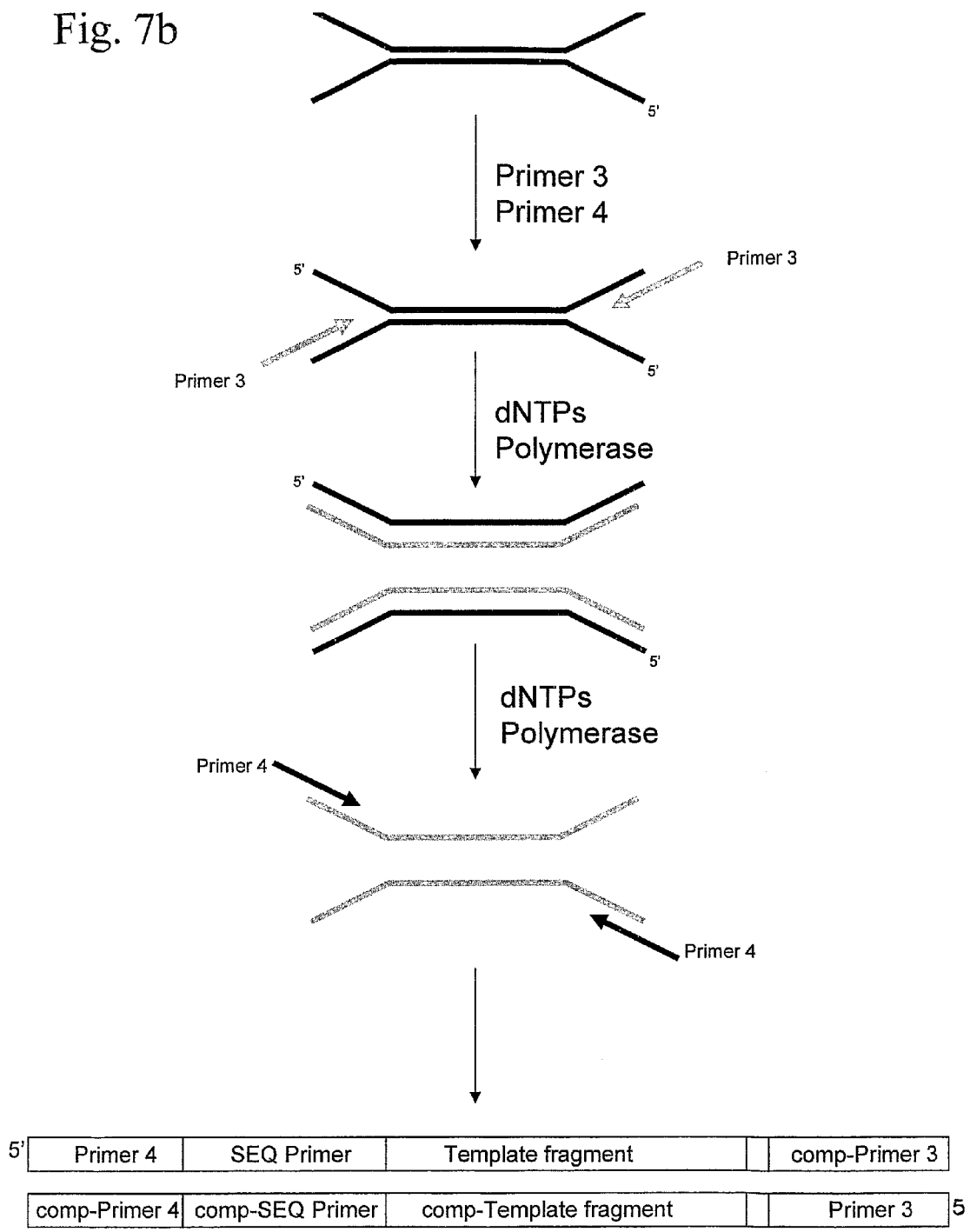

SEQUENCE LISTING

```
<160> NUMBER OF SEQ ID NOS: 23

<210> SEQ ID NO 1
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 1
acactctttc cctacacgac gctcttccga tct                          33

<210> SEQ ID NO 2
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 2
gatcggaaga gctcgtatgc cgtcttctgc ttg                          33

<210> SEQ ID NO 3
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 3
aatgatacgg cgaccaccga gatctacact ctttccctac acga              44

<210> SEQ ID NO 4
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 4
caagcagaag acggcatacg a                                       21

<210> SEQ ID NO 5
<211> LENGTH: 296
<212> TYPE: DNA
<213> ORGANISM: Homo sapiens

<400> SEQUENCE: 5
tgatacggcg accaccgaga tctacactct ttccctacac gacgctcttc cgatctgtgg    60
ggaccgtcct gtgcattgta gggtgttcaa cagcatccct gacctccacc tacaagatgc   120
```

```
cagtagcgaa tcccctcagc cctcatctcc ttgccatagt tgtgtcaacc aaaatcatct    180
ccacacattg ttagatgttt actgggaggc agactcactc ccacttgaga accactgtac    240
tagaaatatc accaagagaa tgagatcgga agagctcgta tgccgtcttc tgcttg        296
```

<210> SEQ ID NO 6
<211> LENGTH: 431
<212> TYPE: DNA
<213> ORGANISM: Homo sapiens

<400> SEQUENCE: 6

```
aatgatacgg cgaccaccga gatctacact ctttccctac acgacgctct tccgatctgt     60
gggctttgtt ctttgagagg ttgcagtcaa catgattctt taagaccaga accctgcaca    120
cttcttgggc tgtatttctt acattccttt tctattttaa ccatatccca tcttacctac    180
ttccagcata gtggtcatat ttaattttta caaaaccatt ttgccacttg ctgccaacta    240
tgttctttat aaagcagact ttgagatgga ggctagtgtt cagaggggat gcttaggaga    300
actttggaga ttaatactta tggcaggtaa gggaaggaag caggattaga cagaaatatt    360
gaactgtgat acaaagtcag caaagacttt agtcaataga tcggaagagc tcgtatgccg    420
tcttctgctt g                                                         431
```

<210> SEQ ID NO 7
<211> LENGTH: 518
<212> TYPE: DNA
<213> ORGANISM: Homo sapiens

<400> SEQUENCE: 7

```
aatgatacgg cgaccaccga gatctacact ctttccctac acgacgctct tccgatcttt     60
cgattccctt caatgattat tccattcgag tacattcgat gattccattc gattctatat    120
gatgatgatt gcattcgagt ccgtgtatta ttccattcca ttccattaga tgattccatt    180
cgagtccatt cgatgattct cttcgattcc gttcgataat tacgcttgat tccgtttgat    240
gttgattcca ttcgagtcca ttcaatgtta attccattcg attctaagcg atgattccat    300
tcctttccat tagaagatga ttccattcga gaccattcga tgattgcatt caactcattc    360
gatgacgatt ccattcaatt ctgttcaatg attccattag attccatttg atgatgagtc    420
cattcgattc catttgatga tgattccatg cgattccatt agatgatgac ccctttcatt    480
tccaagatcg gaagagctcg tatgccgtct ctgcttg                             518
```

<210> SEQ ID NO 8
<211> LENGTH: 387
<212> TYPE: DNA
<213> ORGANISM: Homo sapiens

<400> SEQUENCE: 8

```
aatgatacgg cgaccaccga gatctacact ctttccctac acgacgctct tccgatcttt     60
aaatgctagg catattgtgt accccacatt ggtttgtagc cagctctatg tcatagggcc    120
cttacccttt acctatttat tgttagtata atgtccataa acaagccaat ggctcagcat    180
gaactgatgc taaagaaagc tcatgcctga gtgataaatt aagtgacctc agctatttct    240
cttcagtgtt gtgaaagtta tttttaacag taggtttcct ggtagattct ctaaccactc    300
ggtatttcac atggcccaac ttggttaact cgactggtta cggcaaatgc tgaagatcgg    360
aagagctcgt atgccgtctt ctgcttg                                        387
```

<210> SEQ ID NO 9
<211> LENGTH: 536
<212> TYPE: DNA
<213> ORGANISM: Homo sapiens

<400> SEQUENCE: 9

```
aatgatacgg cgaccaccga gatctacact ctttccctac acgaagctct ccgatcttaa    60
aggaagttag gtagataatt tttgtttagg ccatatagct ttgattttct gataacaatt   120
ttataaactt agaaattttc atgtaagata caggaatact ggaagcaaaa aaagaaggt    180
gctttaacct tagggattga aaaaatagta atttaggttg aaaatgctgc ttgaaagtta   240
atgctgatag cattactaca catgatgatt ttttctggaa ggaaagcttt atctgggcct   300
tcaatttagg aatttttctc tttggttttt aaaagctgcc atattcactt gagcttcatg   360
ggaaagatgc aaataactaa aacaaatgaa caaaaaccat gttgaggtca ggaacttatt   420
tcaagaaagc aagttctagg ttttctttta aagtgacagt agagccttag gcctcaaacc   480
atctacaacc atgttaacag taagatcgga gagctcgta tgccgtcttc tgcttg        536
```

<210> SEQ ID NO 10
<211> LENGTH: 364
<212> TYPE: DNA
<213> ORGANISM: Homo sapiens

<400> SEQUENCE: 10

```
aatgatacgg cgaccaccga gatctacact ctttccctac acgacgctct tcagatcttc    60
ctgcctcagc ctcccgagta gttgggattg caggcatgtg ccaccatgcc ctgctaattt   120
ttgtattttt aactaaagga ggggttttgc catgttggcc aggctggtct tgaatgcctg   180
acctcaggtg atccgcccac ctcagcctcc cagtgctggg attacaggtg tgagccactg   240
cgcccagctg agggtaacta tttttaatgt ggctgatgaa tgtaactatc ctgtcccatg   300
tctctgtccc cagctgcaga gccctcgtcg agatcggaag agctcgtatg ccgtcttctg   360
cttg                                                                364
```

<210> SEQ ID NO 11
<211> LENGTH: 374
<212> TYPE: DNA
<213> ORGANISM: Homo sapiens

<400> SEQUENCE: 11

```
aatgatacgg cgaccaccga gatctacact ctttccctac acgacgctct tccgatctaa    60
ggtttaaatt ttctatatag cctgaaaagt ttgaatgttt aattcaaact aatttattga   120
gcaatggcat ttaagaaaat ggaaagatac aaagggactt tcatcagatg ataagtggat   180
aagagagaaa aatgcagaca gatgagccag agttgtgtaa aagctgggag ctagcaggg    240
ccttgtagat agccaagctg actggggaac agagataaat gggagcagag atcagaaagt   300
tcatccttac cctgctgccc gtggtgaaag gagacttgca agatcggaag agctcgtatg   360
ccgtcttctg cttg                                                     374
```

<210> SEQ ID NO 12
<211> LENGTH: 379
<212> TYPE: DNA
<213> ORGANISM: Homo sapiens

<400> SEQUENCE: 12

```
aatgatacgg cgaccaccga gatctacact ctttccctac acgacgctct tccgatctaa    60
```

```
ggaatcttta ttttctacat ttgagtttgg aaaactgagc tagcacatct aaatccatct    120
aattttggtc attggtttta acaagttcat cttattttt  taaacatctg atctttattt    180
tatagaatag actacacaaa gtcttttgga aaattaaaat attttaactt ccaacaattt    240
tcagatttta cttataaaaa aatttaaaat cctctacttt actcgcatct ttattatttc    300
tgactttcta gctacttaaa gttaaggagg aaattaacct ctctaagatc ggaagagctc    360
gtatgccgtc ttctgcttg                                                 379

<210> SEQ ID NO 13
<211> LENGTH: 455
<212> TYPE: DNA
<213> ORGANISM: Homo sapiens

<400> SEQUENCE: 13
aatgatacgg cgaccaccga gatctacact ctttccctac acgacgctct tccgatctcg     60
ccataaccac agcccaggcc tccgtagcca cagcacccat agccatggcc accattgtag    120
tttctgtagt agctgccaca catggtgttg gttgttgagg tcatccttgg gtaggaagga    180
gtgtaggtga cttcagtatg gacacttctc cgcagagggc ttttatatg  cctcagtgaa    240 tcagaacata gcgtgcccct gcaaaaatat ctctaaaggc ctttcattgt gctgagaagt    300 tctggcccctt acgtatctct ctgatttcat atcctgctac tctcctccat ttatctataa    360
tgctcaaact ctgctggctt tttgtctttt aaaatgcagc aggtttcttc tcacaataag    420
gagatcggaa gagctcgtat gccgtcttct gcttg                               455

<210> SEQ ID NO 14
<211> LENGTH: 495
<212> TYPE: DNA
<213> ORGANISM: Homo sapiens

<400> SEQUENCE: 14
aatgatacgg cgaccaccga gatctacact ctttccctac acgacgctct tccgatctag     60
agagaagtta tttaagacaa gtaaggtatc aggttgtgac tcaaatacca cagaatctag    120
ctattgttag caatattaag tatattttct taaatgaagg attctccatt taccatatgc    180
cccttggata atttccagag aatttaattt tttaaaagga attttcacca attaaattat    240
tgttttgatc aaaagaggac ccactgaaca ccttattcat tattaaaatg tatcataaaa    300
cttaattatg gagctgggta caggggctca tgcctgtaat cccagcactt tgggaggctg    360
aggcaggagg actgcttgag tccaggagtt tgagaccagc ctgggtaaca tggtgaaacc    420
ctgtctctac aaaaaataca aaaaattagc caggtgtggt gagatcggaa gagctcgtat    480
gccgtcttct gcttg                                                     495

<210> SEQ ID NO 15
<211> LENGTH: 491
<212> TYPE: DNA
<213> ORGANISM: Homo sapiens

<400> SEQUENCE: 15
aatgatacgg cgaccaccga gatctacact ctttccctac acgacgctct tccgatctcc     60
cagggaagcc aaaagattgg acacccctct ttcaaactat aaattcctcc catagttagt    120
ttggcctatg ctgggaaatg aacaagggtg gctttgaggt tagaagcaaa atggagtcag    180
ttaggtcaga cttttttca  ctatcatact ttttctatgt cagatttatc tcacttgtaa    240
tttttgcaag ggtggtttca gagccactaa gcttgtggta attttttact gcaatagaaa    300
```

```
actaatgcat taggtaaccc tcttttttc cctctgattg cttgctctgg ggtaagccag    360
ctgccatgtt gaattttca ttttgttact gagcaatcaa tgggctcact gcccgacgtg    420
catagaggcc aatactgtgg cactagtttt tgagaaaaga tcggaagagc tcgtatgccg    480
tcttctgctt g                                                        491

<210> SEQ ID NO 16
<211> LENGTH: 603
<212> TYPE: DNA
<213> ORGANISM: Homo sapiens

<400> SEQUENCE: 16
aatgatacgg cgaccaccga gatctacact cttcccctac acgacgctct ccgatctt     60 tcagatttta tatgtattaa ctcagaacac acacctctta tcacacatat ttttcatgt    120 aatttatcta atcttatag aaaagggtcc atttgcattt tctcttatta gactcctgat    180
ttcaaataat atattactta tgagtatttt tctgtgctgt agttattcat tcttatagat    240
atgtaacata attcctttg caaaggtaaa aattgagcta tctcttgttg aggatttgtt    300
gatctctgtc taaagtttca aaataaaga actttaaaag caaatgtaa attccttca     360 agttttagta aaattacttc aaacttagta gcttaaacaa tacagattta ttatgttaca    420
gttctgtaag acagaaatct gacttgatca caccatggta aaaccaagat actgccaggg    480
ttggtttttt cttgggggg gtctgtggga agagtttgtt tcctttggtt ttccacagcc    540
cagaggctgc ttgcattcct ttgatcacta gatcggaaga gctcgtatgc cgtcttctgc    600
ttg                                                                 603

<210> SEQ ID NO 17
<211> LENGTH: 442
<212> TYPE: DNA
<213> ORGANISM: Homo sapiens

<400> SEQUENCE: 17
aatgatacgg cgaccaccga gatctacact cttcccctac acgacgctct ccgatctta     60 ttgttaggg aataatgaca aggaaaaaaa gtctgtagat attcagtaca gaggcaccca    120 tcttttaaa tttctgaaga ttttttactc atgcttggtt gaatccacag atgcagaacc    180
cataggttca gagggccagc tgtgctttga aaatattagc ttgtgttttt attagaaaga    240
aaactctgag gccaggcacg gtggctcacg cctgtaatcc cagcactttg ggaggctgag    300
gtgggcggat cacaaggtga ggagatcgag accattctgg ctaacatggt gaaaccctgt    360
ctctactaaa aatacaaaaa aattagccgg gcgtggtagt gagcacctag atcggaagag    420
ctcgtatgcc gtcttctgct tg                                            442

<210> SEQ ID NO 18
<211> LENGTH: 537
<212> TYPE: DNA
<213> ORGANISM: Homo sapiens

<400> SEQUENCE: 18
aatgatacgg cgaccaccga gatctacact cttcccctac acgacgctct ccgatctgc     60 aattggtaaa acagtaagca atgaaacaga cacttctcaa atattccaag atggtacacg    120
cttttcagtg tgtatgatcc aataaagcca ttggaagtag ctttaatag tcaaaaaga     180 ctattcagtt agataggaac tatttgccta taactattgg ccaaaaatag gttaaaaaat    240
```

| | |
|---|---:|
| tgttttaaat tgtgctttta caaaacatgt ggactttttt agaaaatgtg tcaaatttca | 300 |
| aaagaaatat agacattatg gaaggtcag ttaagcacag ccctaatcct gaaaacataa | 360 |
| ctatgaaaga tactagctgt tacttgtaac caaaaggaaa aaaagatat tagtaaccaa | 420 |
| taattagcaa acaatgccca tatatttcct tttttttttt ttttttttga cagggggct | 480 |
| tactcaggct ggatgtgatc atgagatcgg aagagctcgt atgccgtctt ctgcttg | 537 |

```
<210> SEQ ID NO 19
<211> LENGTH: 381
<212> TYPE: DNA
<213> ORGANISM: Homo sapiens

<400> SEQUENCE: 19
```

| | |
|---|---:|
| aatgatacgg cgaccaccga gatctacact ctttccctac acgacgctct tccgatcttt | 60 |
| agaagctcta ttatactgga aaagagatat gagacccttc ctactttaag aatcaatgaa | 120 |
| gccgggtgtg gtggctcacg cctgtactcc cagcattttg agaggccaag ctgggcagat | 180 |
| cacctgaggt cgggagtttg agaccagcct agccaacatg atgaaatcct gtttctacta | 240 |
| ataacacaaa aattagccgg gtgtggtggc gcacatctgg aatcccagct actccagagg | 300 |
| ctgaggcagg aaaattgctt gaagctggga agcagaagtt gcagtgaaga tcggaagagc | 360 |
| tcgtatgccg tcttctgctt g | 381 |

```
<210> SEQ ID NO 20
<211> LENGTH: 650
<212> TYPE: DNA
<213> ORGANISM: Homo sapiens

<400> SEQUENCE: 20
```

| | |
|---|---:|
| aatgatacgg cgaccaccga gatctacact ctttccctac acgacgctct tccgatctgg | 60 |
| ctggactgaa taggatagcc ttagctgtaa aattgggctg atctttcaaa tggactcatg | 120 |
| cttgccgaat gactcacgct cctgtttaca atcagctct gtgaagaaat gcagagtggg | 180 |
| aggctctgct tgccagacgg agaccttaga cctccagggg cggagaacgg agtacttcct | 240 |
| ctggtgctcg gcttcccttc ctgggggcag atctctcagc ttctggttgg tggctctcaa | 300 |
| aatccagaca caaggtcagc tgcagccagc gtgggccctg gagtagctcc agttatgggg | 360 |
| cagcaatggc cccctctcat tttgagagct cactttgcct gtggatggtt ttaatccatc | 420 |
| tggataaact tgaggcccat gggaatacca tatactatgg taaccatgta cactgctcta | 480 |
| aagatgtggc tgctgttgta aactttttc ctttattttt gtcaatttcc tattttccag | 540 |
| agtcttgcat acccactatg tctactgtga tagtgaacgt aaaaacatac aagatgttgg | 600 |
| tgttatcctc aatctcagat cggaagagct cgtatgccgt cttctgcttg | 650 |

```
<210> SEQ ID NO 21
<211> LENGTH: 605
<212> TYPE: DNA
<213> ORGANISM: Homo sapiens

<400> SEQUENCE: 21
```

| | |
|---|---:|
| aatgatacgg cgaccaccga gatctacact ctttccctac acgacgctct tccgatctct | 60 |
| gtgagaaatc aatgtctgct gtttataagc cgccgggctg tgatatcctg tgagagtggc | 120 |
| cccagtggat gaagacagat gctctcaagg agcgcagatg acgcgggttc cgaaggactc | 180 |
| ggcacccagc ccggaggccg gcaacatggg caaggggcct ctcacggctg acctgtttcc | 240 |
| tcatcagcac atcaggacaa taagagctcc cacttcacag gtggtgaaga gccaacgtgg | 300 |

```
tgaagaatga ataaagcagc tcgtggaaag tgctgtgcat gaggcctggc aaccggtccc    360
tgctctgagg tcacctgcca cggagctgct gacaggacca ttaaaaacac aattgtgcaa    420
gtgctcaccc acattcacag cagcagaatc tccaccagcc aagcattgga gacgatcctt    480
gcatccatag acatgaacag atgagcaaaa cgtggtctat acggacgatg aaatagcact    540
cagccctaag aagaaataaa atcccgacag agagatcgga gagctcgta tgccgtcttc     600 tgctt                                                                605

<210> SEQ ID NO 22
<211> LENGTH: 439
<212> TYPE: DNA
<213> ORGANISM: Homo sapiens

<400> SEQUENCE: 22
aatgatacgg cgaccaccga gatctacact ctttccctac acgacgctct tccgatctgc    60
tgagaggaga ggagaggctg gcaggggggct gatgcaggag gtgatagggc tcccggtgat   120
aagaggtgag aagaacagtc tctgtgtgcc tagagaagag attaccagaa gtctgctatc    180
tgtttgttcg cggatgtcgg acaggcagga tcggtgatgg caggtcttgg gggaaggatt    240
atcaggagct aaaagctgtc ttcaccttgg ctgctaagaa ctcatctcgg atcttcttag    300
aattccaaat cggacttttc tcctagcagt ggctacatcc ttaacctcaa aaatacccgt    360
attagcagat ctacctccat gaaatagaca attcttgaca aactaagatc ggaagagctc    420
gtatgccgtc ttctgcttg                                                 439

<210> SEQ ID NO 23
<211> LENGTH: 698
<212> TYPE: DNA
<213> ORGANISM: Homo sapiens

<400> SEQUENCE: 23
aatgatacgg cgaccaccga gatctacact ctttccctac acgacgctct tccgatctgt    60 tattttttcat actgatgatt ctagggcggt tccctggact tggctgggac cagaactgtc   120
tcacagctgc cagcgctccc cacccccatg agaaccatcg tgctgaagat gaagagccaa    180
agccaaactg accagcctct gcaaccccaa gcatcaccgt gtgaggacag cgtgatgtgg    240
agccgcggag acccccacgca gtgctgcgag gggcaaccac atgcaggggg gcagaggtgt    300
gggggagcaa gcagatgcca ccggcatgcc taggagccac agggagcatg cgggctgggc    360
agtgatggga atgaacgtga actccagtcc tgccccaaga agtcctccgg ccctccttc     420 tcaattcagg gcacaaagtg gtaactgcag catgcagagg agtcgaggag tcttccctcg    480
tcccaggagc agcacctcgg gcacagtctc ggtcccacag aacagccaag tgtgggttgg    540
tggtctagag acctccgaag atccagtggg ggaaggatgg gcagcagagg gtctactctc    600
tgaaaataag gggaagggat tttcccctccc cactgccaag gtcccagcta ctggacgtgg   660
gtggagatcg gaagagctcg tatgccgtct tctgcctt                            698
```

METHOD OF PREPARING LIBRARIES OF TEMPLATE POLYNUCLEOTIDES

FIELD OF THE INVENTION

The invention relates to a method of preparing a library of template polynucleotides and also the use of the library of templates in methods of solid-phase nucleic acid amplification. In particular, the invention relates to a method of preparing a library of template polynucleotides which have common sequences at their 5' ends and at their 3' ends.

BACKGROUND TO THE INVENTION

Molecular biology and pharmaceutical drug development now make intensive use of nucleic acid analysis. The most challenging areas are whole genome sequencing, single nucleotide polymorphism detection, screening and gene expression monitoring, which typically require analysis of large amounts of nucleic acid.

One area of technology which revolutionised the study of nucleic acids was the development of nucleic acid amplification techniques, such as the polymerase chain reaction (PCR). Amplification reactions, such as PCR, can enable the user to specifically and selectively amplify a particular target nucleic acid of interest from a complex mixture of nucleic acids. However, there is also an ongoing need for nucleic acid amplification techniques which enable simultaneous amplification of complex mixtures of templates of diverse sequence, such as genomic DNA fragments (e.g. "whole genome" amplification) or cDNA libraries, in a single amplification reaction.

PCR amplification cannot occur in the absence of annealing of forward and reverse amplification primers to primer binding sequences in the template to be amplified under the conditions of the annealing steps of the PCR reaction, i.e. if there is insufficient complementarity between primers and template. Some prior knowledge of the sequence of the template is therefore required before one can carry out a PCR reaction to amplify a specific template, unless random primers are used with a consequential loss of specificity. The user must usually know the sequence of at least the primer-binding sites in the template in advance so that appropriate primers can be designed, although the remaining sequence of the template may be unknown. The need for prior knowledge of the sequence of the template increases the complexity and cost of PCR amplification of complex mixtures of templates, such as genomic DNA fragments.

WO 98/44151 and WO 00/18957 both describe methods of forming polynucleotide arrays based on "solid-phase" nucleic acid amplification, which is analogous to a polymerase chain reaction wherein the amplification products are immobilised on a solid support in order to form arrays comprised of nucleic acid clusters or "colonies". Each cluster or colony on such an array is formed from a plurality of identical immobilised polynucleotide strands and a plurality of identical immobilised complementary polynucleotide strands. The arrays so-formed are generally referred to herein as "clustered arrays" and their general features will be further understood by reference to WO 98/44151 or WO 00/18957, the contents of both documents being incorporated herein in their entirety by reference.

As aforesaid, the solid-phase amplification methods of WO 98/44151 and WO 00/18957 are essentially a form of the polymerase chain reaction carried out on a solid support. Like any PCR reaction these methods require the use of forward and reverse amplification primers (which may be identical or different) capable of annealing to a template to be amplified. In the methods of WO 98/44151 and WO 00/18957 both primers are immobilised on the solid support at the 5' end. Other forms of solid-phase amplification are known in which only one primer is immobilised and the other is present in free solution (Mitra, R. D and Church, G. M., Nucleic Acids Research, 1999, Vol. 27, No. 24).

In common with all PCR techniques, solid-phase PCR amplification requires the use of forward and reverse amplification primers which include "template-specific" nucleotide sequences which are capable of annealing to sequences in the template to be amplified, or the complement thereof, under the conditions of the annealing steps of the PCR reaction. The sequences in the template to which the primers anneal under conditions of the PCR reaction may be referred to herein as "primer-binding" sequences.

Certain embodiments of the methods described in WO 98/44151 and WO 00/18957 make use of "universal" primers to amplify templates comprising a variable template portion that it is desired to amplify flanked 5' and 3' by common or "universal" primer binding sequences. The "universal" forward and reverse primers include sequences capable of annealing to the "universal" primer binding sequences in the template construct. The variable template portion may itself be of known, unknown or partially known sequence. This approach has the advantage that it is not necessary to design a specific pair of primers for each template to be amplified; the same primers can be used for amplification of different templates provided that each template is modified by addition of the same universal primer-binding sequences to its 5' and 3' ends. The variable template sequence can therefore be any DNA fragment of interest. An analogous approach can be used to amplify a mixture of templates, such as a plurality or library of template nucleic acid molecules (e.g. genomic DNA fragments), using a single pair of universal forward and reverse primers, provided that each template molecule in the mixture is modified by the addition of the same universal primer-binding, sequences.

Such "universal primer" approaches to PCR amplification, and in particular solid-phase PCR amplification, are advantageous since they enable multiple template molecules of the same or different, known or unknown sequence to be amplified in a single amplification reaction, which may be carried out on a solid support bearing a single pair of "universal" primers. Simultaneous amplification of a mixture of templates of different sequences by PCR would otherwise require a plurality of primer pairs, each pair being complementary to each unique template in the mixture. The generation of a plurality of primer pairs for each individual template is not a viable option for complex mixtures of templates.

The addition of universal priming sequences onto the ends of templates to be amplified by PCR can be achieved by a variety of methods known to those skilled in the art. For example, a universal primer consisting of a universal sequence at its 5' end and a degenerate sequence at its 3' end can be used in a PCR (DOP-PCR, eg PNAS 1996 vol 93 pg 14676-14679) to amplify fragments randomly from a complex template or a complex mixture of templates. The degenerate 3' portion of the primer anneals at random positions on DNA and can be extended to generate a copy of the template that has the universal sequence at its 5' end.

Alternatively, adapters that contain universal priming sequences can be ligated onto the ends of templates. The adapters may be single-stranded or double-stranded. If double-stranded, they may have overhanging ends that are complementary to overhanging ends on the template molecules that have been generated with a restriction endonuclease. Alternatively, the double-stranded adapters may be blunt, in which case the templates are also blunt ended. The blunt ends of the templates may have been formed during a process to shear the DNA into fragments, or they may have been formed by an end repair reaction, as would be well known to those skilled in the art.

A single adapter or two different adapters may be used in a ligation reaction with templates. If a template has been manipulated such that its ends are the same, i.e. both are blunt or both have the same overhang, then ligation of a single compatible adapter will generate a template with that adapter on both ends. However, if two compatible adapters, adapter A and adapter B, are used, then three permutations of ligated products are formed: template with adapter A on both ends, template with adapter B on both ends, and template with adapter A on one end and adapter B on the other end. This last product is, under some circumstances, the only desired product from the ligation reaction and consequently additional purification steps are necessary following the ligation reaction to purify it from the ligation products that have the same adapter at both ends.

The current invention presented herein is a method that uses a single adapter in a ligation reaction to generate a library of template polynucleotides each of which have common, but different, universal primer sequences at their 5' and 3' ends. The method can be applied to preparing simple or complex mixes of templates for amplification, for example a solid surface, using primer sequences, with no prior knowledge of the template sequences. The invention is applicable to the preparation of templates from complex samples such as whole genomes or mixtures of cDNAs, as well as mono-template applications.

SUMMARY OF THE INVENTION

In a first aspect the invention provides a method of generating a library of template polynucleotide molecules which have common sequences at their 5' ends and common sequences at their 3' ends, the method comprising:
ligating identical mismatched adapter polynucleotides to both ends of each of one or more target polynucleotide duplexes to form one or more adapter-target constructs, wherein each mismatched adapter is formed from two annealed polynucleotide strands that form a bimolecular complex comprising at least one double-stranded region and an unmatched region, and
carrying out an initial primer extension reaction in which a primer oligonucleotide is annealed to an adapter portion of each of the adapter-target constructs and extended by sequential addition of nucleotides to form extension products complementary to at least one strand of each of the adapter-target constructs,
wherein the extension products, and optionally amplification products derived therefrom, collectively provide a library of template polynucleotide molecules which have common sequences at their 5' ends and common sequences at their 3' ends.

A second aspect of the invention relates to use of a library of template polynucleotide molecules prepared according to the method of the first aspect of the invention as a template for solid-phase PCR amplification. Thus, in a particular embodiment the invention provides a method of solid-phase nucleic acid amplification of template polynucleotide molecules which comprises:
preparing a library of template polynucleotide molecules which have common sequences at their 5' and 3' ends using the method according to the first aspect of the invention and carrying out a solid-phase nucleic acid amplification reaction wherein said template polynucleotide molecules are amplified.

A third aspect of the invention relates to use of a library of template polynucleotide molecules prepared according to the method of the first aspect of the invention as a template for whole genome amplification. Thus, in a particular embodiment the invention provides a method of whole genome amplification which comprises:
using the method according to the first aspect of the invention to prepare a library of template polynucleotide molecules which have common sequences at their 5' and 3' ends starting from a complex mixture of whole genome fragments and carrying out a whole genome amplification reaction wherein said template polynucleotide molecules are amplified.

In a fourth aspect the invention provides a kit for use in preparing a library of template polynucleotide molecules which have common sequences at their 5' and 3' ends wherein the common sequence at the 5' end of each individual template in the library is not identical and not fully complementary to the common sequence at the 3' end of said template, the kit comprising mismatched adapter polynucleotides as defined herein in relation to the first aspect of the invention and oligonucleotide primers capable of annealing to the mismatched adapter polynucleotides.

BRIEF DESCRIPTION OF THE DRAWINGS

FIG. 1(e) schematically illustrates the sequence components of the two partially complementary strands (denoted oligo A and oligo B) which form the forked adapter when annealed. The 5' end of oligo B is complementary (COMP) to a part of the SEQ PRIMER sequence in oligo A. Oligo A includes a single "T" nucleotide overhang at the 3' end. The 5' end of oligo A is phosphorylated. P represents a terminal phosphate group; X and Y represent surface capture functionalities.

FIG. 2(a) depicts the steps of fragmenting a complex sample such as genomic DNA to generate a plurality of target duplex fragments, ligation of the target duplex fragments to mismatched (forked) adapters to generate adapter-template constructs and removal of unbound adapters. The forked adapter includes a biotin group at the 5' end which is not ligated to the target fragment to facilitate solid-phase capture of the adapter-target constructs, e.g. onto streptavidin magnetic beads. FIG. 2(b) depicts an initial primer extension reaction in which primers are annealed to mismatched adapter regions on each strand of an adapter-target construct and extended to generate extension products complementary to each strand of the adapter-target construct. For simplicity the ligation and primer extension steps are illustrated for a single adapter-target construct.

FIG. 6(e) schematically illustrates the component sequences present in the two strands (denoted oligo C and oligo B) which form the adapter when annealed. P represents a terminal phosphate group; X and Y represent surface capture functionalities.

FIGS. 7a and 7b illustrate a still further embodiment of the invention based on use of the forked adapters illustrated in FIG. 6. FIG. 7(a) depicts fragmentation and ligation steps substantially similar to those illustrated in FIG. 5. FIG. 7(b) depicts subsequent PCR amplification using "tailed" PCR primers which have 3' end sequences complementary to a sequence at the 5' end of the adapter, and schematically illustrates the sequence composition of the double-stranded amplification products formed in the PCR reaction. For simplicity the ligation and PCR amplification steps are illustrated for a single adapter-target construct.

FIG. 9(a) depicts fragmentation, ligation and subsequent removal of unbound adapters.

DETAILED DESCRIPTION OF THE INVENTION

Figure 1:
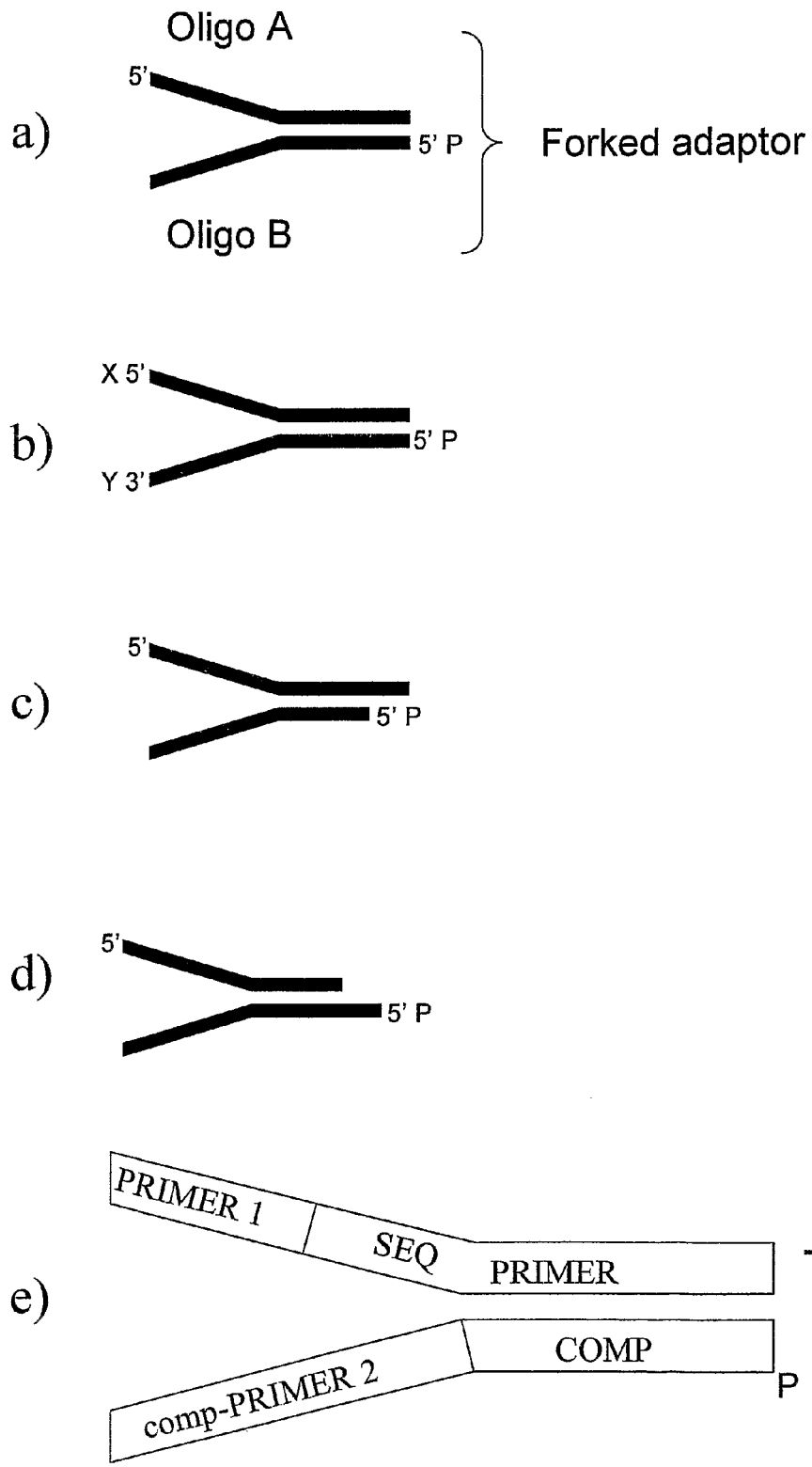
FIG. 1 illustrates several examples of forked mismatched adapters for use in the method of the invention, specifically depicting different overhanging or blunt end structures permissible at the "ligatable" end of the adapter.

In its first aspect the invention provides a method of generating a library of template polynucleotide molecules which have common sequences at their 5' and 3' ends. In this context the term "common" is interpreted as meaning common to all templates in the library. As explained in further detail below, all templates within the library will contain regions of common sequence at (or proximal to) their 5' and 3' ends, wherein the common sequence at the 5' end of each individual template in the library is not identical and not fully complementary to the common sequence at the 3' end of said template.

The term "library" merely refers to a collection or plurality of template molecules which share common sequences at their 5' ends and common sequences at their 3' ends. Use of the term "library" to refer to a collection or plurality of template molecules should not be taken to imply that the templates making up the library are derived from a particular source, or that the "library" has a particular composition. By way of example, use of the term "library" should not be taken to imply that the individual templates within the library must be of different nucleotide sequence or that the templates be related in terms of sequence and/or source.

In it's various embodiments the invention encompasses formation of so-called "monotemplate" libraries, which comprise multiple copies of a single type of template molecule, each having common sequences at their 5' ends and their 3' ends, as well as "complex" libraries wherein many, if not all, of the individual template molecules comprise different target sequences (as defined below), although all share common sequences at their 5' ends and 3' ends. Such complex template libraries may be prepared using the method of the invention starting from a complex mixture of target polynucleotides such as (but not limited to) random genomic DNA fragments, cDNA libraries etc. The invention also extends to "complex" libraries formed by mixing together several individual "monotemplate" libraries, each of which has been prepared separately using the method of the invention starting from a single type of target molecule (i.e. a monotemplate). In preferred embodiments more than 50%, or more than 60%, or more than 70%, or more than 80%, or more than 90%, or more than 95% of the individual polynucleotide templates in a complex library may comprise different target sequences, although all templates in a given library will share common sequence at their 5' ends and common sequence at their 3' ends.

Use of the term "template" to refer to individual polynucleotide molecules in the library merely indicates that one or both strands of the polynucleotides in the library are capable of acting as templates for template-dependent nucleic-acid polymerisation catalysed by a polymerase. Use of this term should not be taken as limiting the scope of the invention to libraries of polynucleotides which are actually used as templates in a subsequent enzyme-catalysed polymerisation reaction.

The library is formed by ligating identical adapter polynucleotide molecules ("mismatched adapters", the general features of which are defined below) to the 5' and 3' ends of one or more target polynucleotide duplexes (which may be of known, partially known or unknown sequence) to form adapter-target constructs and then carrying out an initial primer extension reaction in which extension products complementary to both strands of each individual adapter-target construct are formed. The resulting primer extension products, and optionally amplified copies thereof, collectively provide a library of template polynucleotides.

Each strand of each template molecule in the library formed in the primer extension reaction will therefore have the following structure, when viewed as a single strand:

5'-[common sequence I]-[target sequence]-[common sequence II]-3' wherein "common sequence I" represents a sequence derived from copying a first strand of the mismatched adapter and is common to all template molecules in the library generated in the initial primer extension reaction;

"target" represents a sequence derived from one strand of the target polynucleotide duplex and may be different in different individual template molecules within the library; and "common sequence II" represents a sequence derived from copying of a second strand of the mismatched adapter and is also common to all template molecules in the library generated in the initial primer extension reaction.

Since "common sequence I" and "common sequence II" are common to all template strands in the library they may include "universal" primer-binding sequences, enabling all templates in the library to be ultimately amplified in a solid-phase PCR procedure using universal primers.

It is a key feature of the invention, however, that the common 5' and 3' end sequences denoted "common sequence I" and "common sequence II" are not fully complementary to each other, meaning that each individual template strand can contain different (and non-complementary) universal primer sequences at its 5' and 3' ends.

It is generally advantageous for complex libraries of templates to be amplified by PCR (e.g. whole genome amplification) whether performed in solution or on a solid support, to include regions of "different" sequence at their 5' and 3' ends, which are nevertheless common to all template molecules in the library, especially if the amplification products are to be ultimately sequenced. For example, the presence of common unique sequence at one end only of each template in the library can provide a binding site for a sequencing primer, enabling one strand of each template in the amplified form of the library to be sequenced in a single sequencing reaction using a single type of sequencing primer.

Typically "common sequence I" and "common sequence II" will consist of no more than 100, or no more than 50, or no more than 40 consecutive nucleotides at the 5' and 3' ends, respectively, of each strand of each template polynucleotide. The precise length of the two sequences may or may not be identical. The nucleotide sequences of "common sequence I" and "common sequence II" in the template polynucleotides will be determined in part by the sequences of the adapter strands ligated to the target polynucleotides and in part by the sequence of the primer used in the initial primer extension reaction, and any subsequent rounds of nucleic acid amplification.

In embodiments wherein the initial primer extension product is subjected to further amplification by conventional PCR, then the products of the amplification reaction will be double-stranded polynucleotides, one strand of which has the structure:

5'-[common sequence I]-[target sequence]-[common sequence II]-3'

It will be appreciated that "common sequence II" in the amplification products may differ somewhat to the "common sequence II" present in the products of the initial primer extension reaction, since the former will be determined in part by the sequence of the PCR primer used to prime synthesis of a polynucleotide strand complementary to the initial primer extension product, whereas the latter will be determined solely by copying of the adapter sequences at the 3' ends of the adapter-template constructs in the initial primer extension. Nevertheless, since the PCR primer is designed to anneal to a sequence in the initial extension products which is complementary to the 3' adapter, the two forms of "common sequence II" will contain identical sequence, at least at the 3' end. Additional sequence may be included at the 5' end of "common sequence II" in the amplified products, for example by the use of "tailed" PCR primers, as described in detail below. In other embodiments the common sequences present in the amplification products may actually be shorter than the common sequences including in the adapters originally ligated to the target.

The precise nucleotide sequences of the common regions of the template molecules in the library are generally not material to the invention and may be selected by the user. The common sequences must at least comprise "primer-binding" sequences which enable specific annealing of amplification primers when the templates are in use in a solid-phase amplification reaction. The primer-binding sequences are thus determined by the sequence of the primers to be ultimately used for solid-phase amplification. The sequence of these primers in turn is advantageously selected to avoid or minimise binding of the primers to the target portions of the templates within the library under the conditions of the amplification reaction, but is otherwise not particularly limited. By way of example, if the target portions of the templates are derived from human genomic DNA, then the sequences of the primers to be used in solid phase amplification should ideally be selected to minimise non-specific binding to any human genomic sequence.

The adapter polynucleotides used in the method of the invention are referred to herein as "mismatched" adapters because, as will be explained in detail herein, it is essential that the adapters include a region of sequence mismatch, i.e. they must not be formed by annealing of fully complementary polynucleotide strands.

Mismatched adapters for use in the invention are formed by annealing of two partially complementary polynucleotide strands so as to provide, when the two strands are annealed, at least one double-stranded region and at least one unmatched region.

The "double-stranded region" of the adapter is a short double-stranded region, typically comprising 5 or more consecutive base pairs, formed by annealing of the two partially complementary polynucleotide strands. This term simply refers to a double-stranded region of nucleic acid in which the two strands are annealed and does not imply any particular structural conformation.

Generally it is advantageous for the double-stranded region to be as short as possible without loss of function. By "function" in this context is meant that the double-stranded region form a stable duplex under standard reaction conditions for an enzyme-catalysed nucleic acid ligation reaction, which will be well known to the skilled reader (e.g. incubation at a temperature in the range of from 4° C. to 25° C. in a ligation buffer appropriate for the enzyme), such that the two strands forming the adapter remain partially annealed during ligation of the adapter to a target molecule. It is not absolutely necessary for the double-stranded region to be stable under the conditions typically used in the annealing steps of primer extension or PCR reactions.

Since identical adapters are ligated to both ends of each template molecule, the target sequence in each adapter-target construct will be flanked by complementary sequences derived from the double-stranded region of the adapters. The longer the double-stranded region, and hence the complementary sequences derived therefrom in the adapter-target constructs, the greater the possibility that the adapter-target construct is able to fold back and base-pair to itself in these regions of internal self-complementarity under the annealing conditions used in primer extension and/or PCR. Generally it is preferred for the double-stranded region to be 20 or less, 15 or less, or 10 or less base pairs in length in order to reduce this effect. The stability of the double-stranded region may be increased, and hence its length potentially reduced, by the inclusion of non-natural nucleotides which exhibit stronger base-pairing than standard Watson-Crick base pairs.

It is preferred, but not absolutely essential, for the two strands of the adapter to be 100% complementary in the double-stranded region. It will be appreciated that one or more nucleotide mismatches may be tolerated within the double-stranded region, provided that the two strands are capable of forming a stable duplex under standard ligation conditions.

Adapters for use in the invention will generally include a double-stranded region adjacent to the "ligatable" end of the adapter, i.e. the end that is joined to a target polynucleotide in the ligation reaction. The ligatable end of the adapter may be blunt or, in other embodiments, short 5' or 3' overhangs of one or more nucleotides may be present to facilitate/promote ligation. The 5' terminal nucleotide at the ligatable end of the adapter should be phosphorylated to enable phosphodiester linkage to a 3' hydroxyl group on the target polynucleotide.

The term "unmatched region" refers to a region of the adapter wherein the sequences of the two polynucleotide strands forming the adapter exhibit a degree of non-complementarity such that the two strands are not capable of annealing to each other under standard annealing conditions for a primer extension or PCR reaction. The two strands in the unmatched region may exhibit some degree of annealing under standard reaction conditions for a enzyme-catalysed ligation reaction, provided that the two strands revert to single stranded form under annealing conditions.

The conditions encountered during the annealing steps of a PCR reaction will be generally known to one skilled in the art, although the precise annealing conditions will vary from reaction to reaction (see Sambrook et al., 2001, *Molecular Cloning, A Laboratory Manual*, 3rd Ed, Cold Spring Harbor Laboratory Press, Cold Spring Harbor Laboratory Press, NY; Current Protocols, eds Ausubel et al.). Typically such conditions may comprise, but are not limited to, (following a denaturing step at a temperature of about 94° C. for about one minute) exposure to a temperature in the range of from 40° C. to 72° C. (preferably 50-68° C.) for a period of about 1 minute in standard PCR reaction buffer.

Different annealing conditions may be used for a single primer extension reaction not forming part of a PCR reaction (again see Sambrook et al., 2001, *Molecular Cloning, A Laboratory Manual*, 3rd Ed, Cold Spring Harbor Laboratory Press, Cold Spring Harbor Laboratory Press, NY; Current Protocols, eds Ausubel et al.). Conditions for primer annealing in a single primer extension include, for example, exposure to a temperature in the range of from 30 to 37° C. in standard primer extension buffer. It will be appreciated that different enzymes, and hence different reaction buffers, may be used for a single primer extension reaction as opposed to a PCR reaction. There is no requirement to use a thermostable polymerase for a single primer extension reaction.

It is to be understood that the "unmatched region" is provided by different portions of the same two polynucleotide strands which form the double-stranded region(s). However, the portions of the two strands forming the unmatched, region are not annealed under conditions in which other portions of the same two strands are annealed to form one or more double-stranded regions. For avoidance of doubt it is to be understood that a single-stranded or single base overhang at the 5' or 3' end of a polynucleotide duplex does not constitute an "unmatched region" in the context of this invention.

The portions of the two strands forming the double-stranded region typically comprise at least 10, or at least 15, or at least 20 consecutive nucleotides on each strand. The lower limit on the length of the unmatched region will typically be determined by function, for example the need to provide a suitable sequence for binding of a primer for primer extension, PCR and/or sequencing. Theoretically there is no upper limit on the length of the unmatched region, except that it general it is advantageous to minimise the overall length of the adapter, for example in order to facilitate separation of unbound adapters from adapter-target constructs following the ligation step. Therefore, it is preferred that the unmatched region should be less than 50, or less than 40, or less than 30, or less than 25 consecutive nucleotides in length on each strand.

The overall length of the two strands forming the adapter will typically in the range of from 25 to 100 nucleotides, more typically from 30 to 55 nucleotides.

The portions of the two strands forming the unmatched region should preferably be of similar length, although this is not absolutely essential, provided that the length of each portion is sufficient to fulfil its desired function (e.g. primer binding). The inventors' have shown by experiment that the portions of the two strands forming the unmatched region may differ by up to 25 nucleotides without unduly affecting adapter function.

Most preferably the portions of the two polynucleotide strands forming the unmatched region will be completely mismatched, or 100% non-complementary. However, skilled readers will be appreciate that some sequence "matches", i.e. a lesser degree of non-complementarity may be tolerated in this region without affecting function to a material extent. As aforesaid, the extent of sequence mismatching or non-complementarity must be such that the two strands in the unmatched region remain in single-stranded form under annealing conditions as defined above.

The precise nucleotide sequence of the adapters is generally not material to the invention and may be selected by the user such that the desired sequence elements are ultimately included in the common sequences of the library of templates derived from the adapters, for example to provide binding sites for particular sets of universal amplification primers and/or sequencing primers. Additional sequence elements may be included, for example to provide binding sites for sequencing primers which will ultimately be used in sequencing of template molecules in the library, or products derived from amplification of the template library, for example on a solid support. The adapters may further include "tag" sequences, which can be used to tag or mark template molecules derived from a particular source. The general features and use of such tag sequences is described in the applicant's pending application published as WO 05/068656.

Although the precise nucleotide sequence of the adapter is generally non-limiting to the invention, the sequences of the individual strands in the unmatched region should be such that neither individual strand exhibits any internal self-complementarity which could lead to self-annealing, formation of hairpin structures etc. under standard annealing conditions. Self-annealing of a strand in the unmatched region is to be avoided as it may prevent or reduce specific binding of an amplification primer to this strand.

The mismatched adapters are preferably formed from two strands of DNA, but may include mixtures of natural and non-natural nucleotides (e.g. one or more ribonucleotides) linked by a mixture of phosphodiester and non-phosphodiester backbone linkages. Other non-nucleotide modifications may be included such as, for example, biotin moieties, blocking groups and capture moieties for attachment to a solid surface, as discussed in further detail below.

The one or more "target polynucleotide duplexes" to which the adapters are ligated may be any polynucleotide molecules that it is desired to amplify by solid-phase PCR, generally with a view to sequencing. The target polynucleotide duplexes may originate in double-stranded DNA form (e.g. genomic DNA fragments) or may have originated in single-stranded form, as DNA or RNA, and been converted to dsDNA form prior to ligation. By way of example, mRNA molecules may be copied into double-stranded cDNAs suitable for use in the method of the invention using standard techniques well known in the art. The precise sequence of the target molecules is generally not material to the invention, and may be known or unknown. Modified DNA molecules including non-natural nucleotides and/or non-natural backbone linkages could serve as the target, provided that the modifications do not preclude adapter ligation and/or copying in a primer extension reaction.

Although the method could in theory be applied to a single target duplex (i.e. one individual double-stranded molecule), it is preferred to use a mixture or plurality of target polynucleotide duplexes. The method of the invention may be applied to multiple copies of the same target molecule (so-called monotemplate applications) or to a mixture of different target molecules which differ from each other with respect to nucleotide sequence over all or a part of their length, e.g. a complex mixture of templates. The method may be applied to a plurality of target molecules derived from a common source, for example a library of genomic DNA fragments derived from a particular individual. In a preferred embodiment the target polynucleotides will comprise random fragments of human genomic DNA. The fragments may be derived from a whole genome or from part of a genome (e.g. a single chromosome or sub-fraction thereof), and from one individual or several individuals. The DNA target molecules may be treated chemically or enzymatically either prior to, or subsequent to the ligation of the adaptor sequences. Techniques for fragmentation of genomic DNA include, for example, enzymatic digestion or mechanical shearing.

"Ligation" of adapters to 5' and 3' ends of each target polynucleotide involves joining of the two polynucleotide strands of the adapter to double-stranded target polynucleotide such that covalent linkages are formed between both strands of the two double-stranded molecules. In this context "joining" means covalent linkage of two polynucleotide strands which were not previously covalently linked. Preferably such "joining" will take place by formation of a phosphodiester linkage between the two polynucleotide strands but other means of covalent linkage (e.g. non-phosphodiester backbone linkages) may be used. However, it is an essential requirement that the covalent linkages formed in the ligation reactions allow for read-through of a polymerase, such that the resultant construct can be copied in a primer extension reaction using primers which binding to sequences in the regions of the adapter-target construct that are derived from the adapter molecules.

The ligation reactions will preferably be enzyme-catalysed. The nature of the ligase enzyme used for enzymatic ligation is not particularly limited. Non-enzymatic ligation techniques (e.g. chemical ligation) may also be used, provided that the non-enzymatic ligation leads to the formation of a covalent linkage which allows read-through of a polymerase, such that the resultant construct can be copied in a primer extension reaction.

The desired products of the ligation reaction are adapter-target constructs in which identical adapters are ligated at both ends of each target polynucleotide, given the structure adapter-target-adapter. Conditions of the ligation reaction should therefore be optimised to maximise the formation of this product, in preference to targets having an adapter at one end only.

The products of the ligation reaction may be subjected to purification steps in order to remove unbound adapter molecules before the adapter-target constructs are processed further. Any suitable technique may be used to remove excess unbound adapters, preferred examples of which will be described in further detail below.

Adapter-target constructs formed in the ligation reaction are then subject to an initial primer extension reaction in which a primer oligonucleotide is annealed to an adapter portion of each of the adapter-target constructs and extended by sequential addition of nucleotides to the free 3' hydroxyl end of the primer to form extension products complementary to at least one strand of each of the adapter-target constructs.

The term "initial" primer extension reaction refers to a primer extension reaction in which primers are annealed directly to the adapter-target constructs, as opposed to either complementary strands formed by primer extension using the adapter-target construct as a template or amplified copies of the adapter-target construct. It is a key feature of the method of the invention that the initial primer extension reaction is carried out using a "universal" primer which binds specifically to a cognate sequence within an adapter portion of the adapter-target construct, and is not carried out using a target-specific primer or a mixture of random primers. The use of an adapter-specific primer for the initial primer extension reaction is key to formation of a library of templates which have common sequence at the 5' and common sequence at the 3' end.

The primers used for the initial primer extension reaction will be capable of annealing to each individual strand of adapter-target constructs having adapters ligated at both ends, and can be extended so as to obtain two separate primer extension products, one complementary to each strand of the construct. Thus, in the most preferred embodiment the initial primer extension reaction will result in formation of primer extension products complementary to each strand of each adapter-target In a preferred embodiment the primer used in the initial primer extension reaction will anneal to a primer-binding sequence (in one strand) in the unmatched region of the adapter.

The term "annealing" as used in this context refers to sequence-specific binding/hybridisation of the primer to a primer-binding sequence in an adapter region of the adapter-target construct under the conditions to be used for the primer annealing step of the initial primer extension reaction.

The products of the primer extension reaction may be subjected to standard denaturing conditions in order to separate the extension products from strands of the adapter-target constructs. Optionally the strands of the adapter-target constructs may be removed at this stage. The extension products (with or without the original strands of the adapter-target constructs) collectively form a library of template polynucleotides which can be used as templates for solid-phase PCR.

If desired, the initial primer extension reaction may be repeated one or more times, through rounds of primer annealing, extension and denaturation, in order to form multiple copies of the same extension products complementary to the adapter-target constructs.

In other embodiments the initial extension products may be amplified by convention solution-phase PCR, as described in further detail below. The products of such further PCR amplification may be collected to form a library of templates comprising "amplification products derived from" the initial primer extension products. In a preferred embodiment both primers used for further PCR amplification will anneal to different primer-binding sequences on opposite strands in the unmatched region of the adapter. Other embodiments may, however, be based on the use of a single type of amplification primer which anneals to a primer-binding sequence in the double-stranded region of the adapter. In embodiments of the method based on PCR amplification the "initial" primer extension reaction occurs in the first cycle of PCR.

Inclusion of the initial primer extension step (and optionally further rounds of PCR amplification) to form complementary copies of the adapter-target constructs (prior to whole genome or solid-phase PCR) is advantageous, for several reasons. Firstly, inclusion of the primer extension step, and subsequent PCR amplification, acts as an enrichment step to select for adapter-target constructs with adapters ligated at both ends. Only target constructs with adapters ligated at both ends provide effective templates for whole genome or solid-phase PCR using common or universal primers specific for primer-binding sequences in the adapters, hence it is advantageous to produce a template library comprising only double-ligated targets prior to solid-phase or whole genome amplification.

Secondly, inclusion of the initial primer extension step, and subsequent PCR amplification, permits the length of the common sequences at the 5' and 3' ends of the target to be increased prior to solid-phase or whole genome PCR. As outlined above, it is generally advantageous for the length of the adapter molecules to be kept as short as possible, to maximise the efficiency of ligation and subsequent removal of unbound adapters. However, for the purposes of whole genome or solid-phase PCR it may be an advantage to have longer sequences common or "universal" sequences at the 5' and 3' ends of the templates to be amplified. Inclusion of the primer extension (and subsequent amplification) steps means that the length of the common sequences at one (or both) ends of the polynucleotides in the template library can be increased after ligation by inclusion of additional sequence at the 5' ends of the primers used for primer extension (and subsequent amplification). The use of such "tailed" primers is described in further detail below.

Various non-limiting specific embodiments of the method of the invention will now be described in further detail with reference to the accompanying drawings. Features described as being preferred in relation to one specific embodiment of the invention apply mutatis mutandis to other specific embodiments of the invention unless stated otherwise.

FIG. 1 illustrates several embodiments of a particular type of mismatched adapter for use in the method of the invention. The adapter is formed by annealing two single-stranded oligonucleotides, herein referred to as "oligo A" and "oligo B". Oligo A and oligo B may be prepared by conventional automated oligonucleotide synthesis techniques in routine use in the art. The oligonucleotides are partially complementary such that the 3' end of oligo A is complementary to the 5' end of oligo B. The 5' end of oligo A and the 3' end of oligo B are not complementary to each other. When the two strands are annealed, the resulting structure is double stranded at one end (the double-stranded region) and single stranded at the other end (the unmatched region) and is referred to herein as a "forked adapter" (FIG. 1a). The double-stranded region of the forked adapter may be blunt-ended (FIG. 1b) or it may have an overhang. In the latter case, the overhang may be a 3' overhang (FIG. 1c) or a 5' overhang (FIG. 1d), and may comprise a single nucleotide or more than one nucleotide.

The 5' end of the double-stranded part of the forked adapter is phosphorylated, i.e. the 5' end of oligo B (FIG. 1a-d). The presence of the 5' phosphosphate group identifies this as the "ligatable" end of the adapter. The 5' end of oligo A may be biotinylated or bear another functionality (represented by X) that enables it to be captured on a surface, such as a bead. Such alternative functionalities other than biotin are known to those skilled in the art. The 3' end of oligo B may also be biotinylated or bear another functionality (represented by Y) that enables it to be captured on a surface (FIG. 1d).

The phosphodiester bonds that comprise the back-bone of the oligonucleotides may be replaced with non-enzymatically cleavable bonds such as phosphorothioate bonds. Preferably only the last, or last and penultimate, phosphodiester bonds at both the 3' and 5' ends of the oligonucleotides will be substituted with phosphorothioate bonds. In the most preferred embodiment of the invention, oligo A contains a biotin group on its 5' end, oligo B is phosphorylated at its 5' end and the double-stranded portion of the duplex contains a single base 3' overhang comprising a 'T' nucleotide. Oligo A consists of two sequences: a sequence at the 5' end which is identical to that of a universal primer to be used for PCR amplification, referred to herein as "PRIMER 1" sequence, and at its 3' end a sequence identical to that of a universal sequencing primer, herein referred to herein as "SEQ PRIMER" sequence, plus an additional 'T' nucleotide on the 3' end. Oligo B also consists of two sequences: a sequence at its 5' end that is complementary to only part of the 3' end of the SEQ PRIMER sequence in Oligo A, excluding the 'T' overhang of Oligo A, and a sequence complementary to that of a universal PCR amplification primer, herein referred to as "comp-PRIMER 2" at its 3' end (FIG. 1e).

FIG. 2 illustrates one embodiment of the method of the invention based on use of the forked adapters illustrated in FIG. 1. A mixture of target DNA molecules of different sequence may be prepared by mixing a number, greater than one, of individual DNA molecules. In the preferred procedure, genomic DNA is fragmented into small molecules, preferably less than 1000 base pairs in length. Fragmentation of DNA may be achieved by a number of methods including: enzymatic digestion, chemical cleavage, sonication, nebulisation, or hydroshearing, preferably nebulisation.

Fragmented DNA may be made blunt-ended by a number of methods known to those skilled in the art. In the preferred method, the ends of the fragmented DNA are end repaired with T4 DNA polymerase and Klenow polymerase, a procedure well known to those skilled in the art, and then phosphorylated with a polynucleotide kinase enzyme. A single 'A' deoxynucleotide is then added to both 3' ends of the DNA molecules using Taq polymerase enzyme, producing a one-base 3' overhang that is complementary to the one-base 3"T' overhang on the double-stranded end of the forked adapter.

Figure 2A:
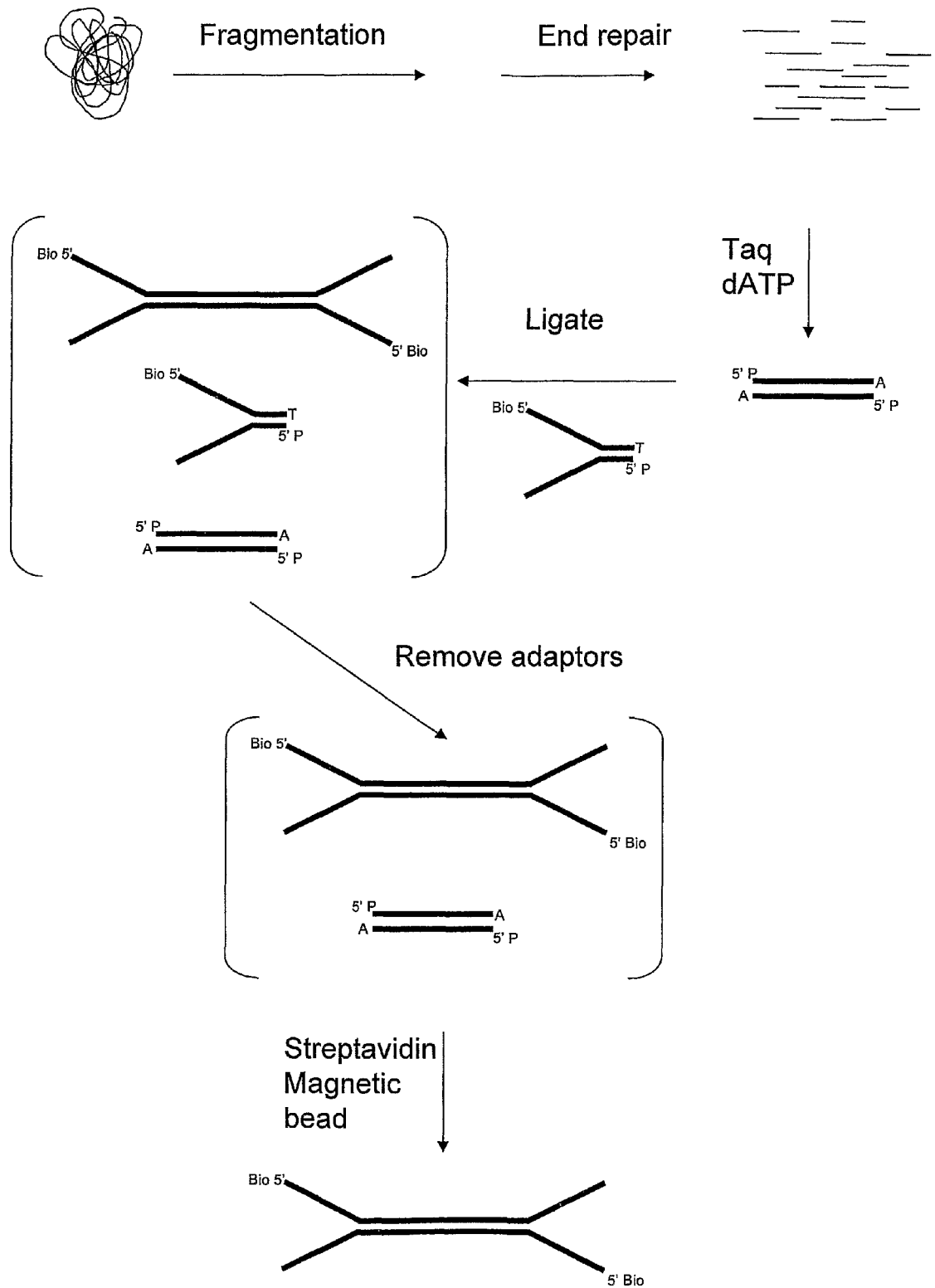
FIGS. 2a and 2b illustrate one embodiment of the method of the invention based on use of the forked adapters illustrated in FIG. 1.

A ligation reaction between the forked adapter and the DNA fragments is then performed using a suitable ligase enzyme (e.g. T4 DNA ligase) which joins two copies of the adapter to each DNA fragment, one at either end, to form adapter-target constructs. The products of this reaction can be purified from unligated adapter by a number of means, including size-inclusion chromatography, preferably by electrophoresis through an agarose gel slab followed by excision of a portion of the agarose that contains the DNA greater in size that the size of the adapter (FIG. 2a).

After the excess adapter has been removed, unligated target DNA remains in addition to ligated adapter-target constructs and this can be removed by selectively capturing only those target DNA molecules that have adapter attached. The presence of a biotin group on the 5' end of Oligo A of the adapter enables any target DNA ligated to the adapter to be captured on a surface coated with streptavidin, a protein that selectively and tightly binds biotin. Streptavidin can be coated onto a surface by means known to those skilled in the art. In the preferred method, commercially available magnetic beads that are coated in streptavidin can be used to capture ligated adapter-target constructs. The application of a magnet to the side of a tube containing these beads immobilises them such that they can be washed free of the unligated target DNA molecules (FIG. 2a).

An oligonucleotide, herein referred to as PRIMER 2, which hybridises to the "comp-PRIMER 2" sequence on the oligo B strand of the adapter-target constructs can be used in an initial primer extension reaction to generate a complementary copy of the adapter-target strand attached to the bead.

Figure 2B:
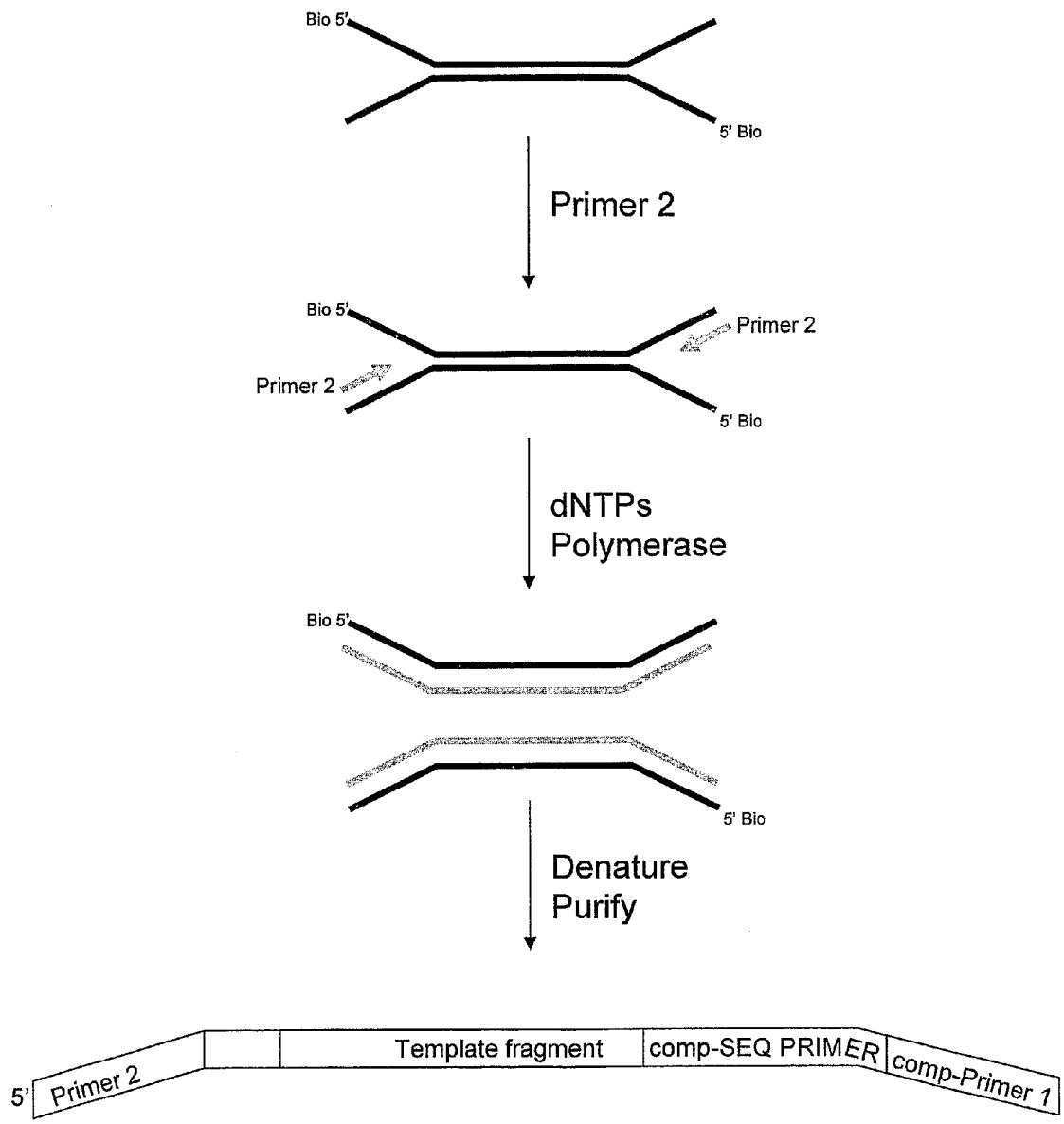

The resulting primer extension product forms a double-stranded duplex with its complementary adapter-target strand attached to the bead and it can then be isolated and purified from adapter-target strand on the bead by denaturation (FIG. 2b).

There are several standard methods for separating the strand of a DNA duplex by denaturation, including thermal denaturation, or preferably chemical denaturation in 100 mM sodium hydroxide solution. The pH of a solution of single-stranded DNA in a sodium hydroxide collected from the supernatant of a suspension of magnetic beads can be neutralised by adjusting with an appropriate solution of acid, or preferably by buffer-exchange through a size-exclusion chromatography column pre-equilibrated in a buffered solution. The resulting solution contains a library of single-stranded DNA template molecules all of which comprise in order: 5' PRIMER 2 sequence, target DNA, the complement of SEQ PRIMER sequence, then the complement of PRIMER 1 sequence. This template library can then be used for solid-phase PCR amplification using immobilised PRIMER 1 and PRIMER 2 oligonucleotides. It will be appreciated, however, that the utility of the library is not limited to solid-phase PCR but extends to any type of PCR amplification, including whole-genome amplification performed entirely in solution.

Figure 3:
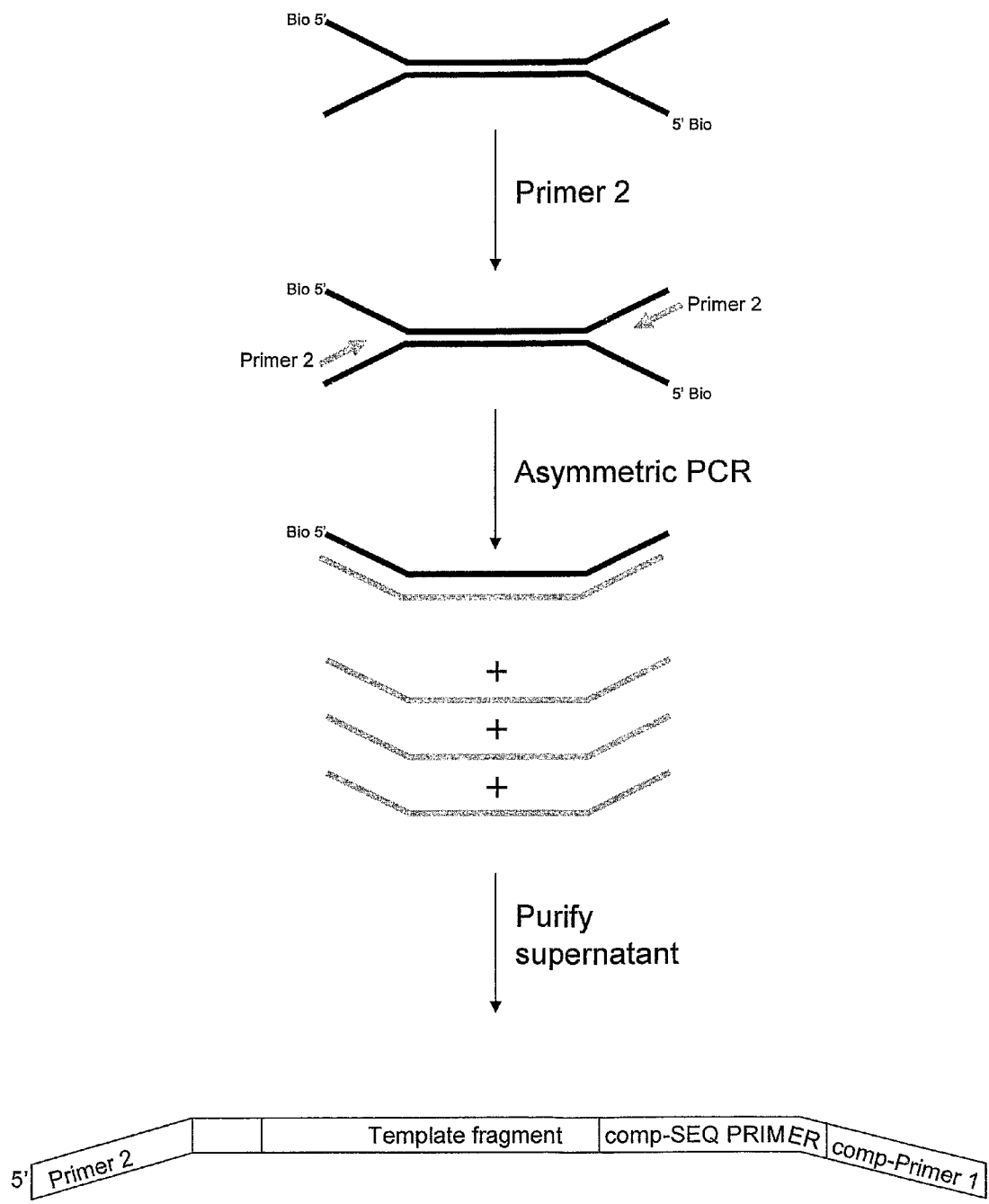
FIG. 3 illustrates an alternative embodiment of the invention in which adapter-target constructs are subjected to multiple rounds of primer annealing and extension to generate multiple single-stranded copies of each adapter-target construct. For simplicity the primer extension steps are illustrated for a single adapter-target construct.

FIG. 3 illustrates an alternative embodiment of the invention in which adapter-target constructs prepared as described above with reference to FIG. 2 are subjected to multiple rounds of primer annealing and extension to generate multiple single-stranded copies of each adapter-target construct. In this embodiment of the invention, the initial primer extension reaction on the bead-immobilised adapter-template molecules with PRIMER 2 is in effect replaced with an asymmetric PCR amplification with the PRIMER 2 oligonucleotide (FIG. 3), this being equivalent to multiple rounds of the same primer extension reaction. In this embodiment, multiple single-stranded copies of the bead-immobilised strands are generated in the supernatant of the bead suspension due to PCR thermocycling, hence a separate denaturation step is not necessary to recover the newly synthesised complementary copies of the bead-immobilised adapter-target strands; the copies can be purified from the supernatant by standard methods, known to those skilled in the art.

Figure 4:
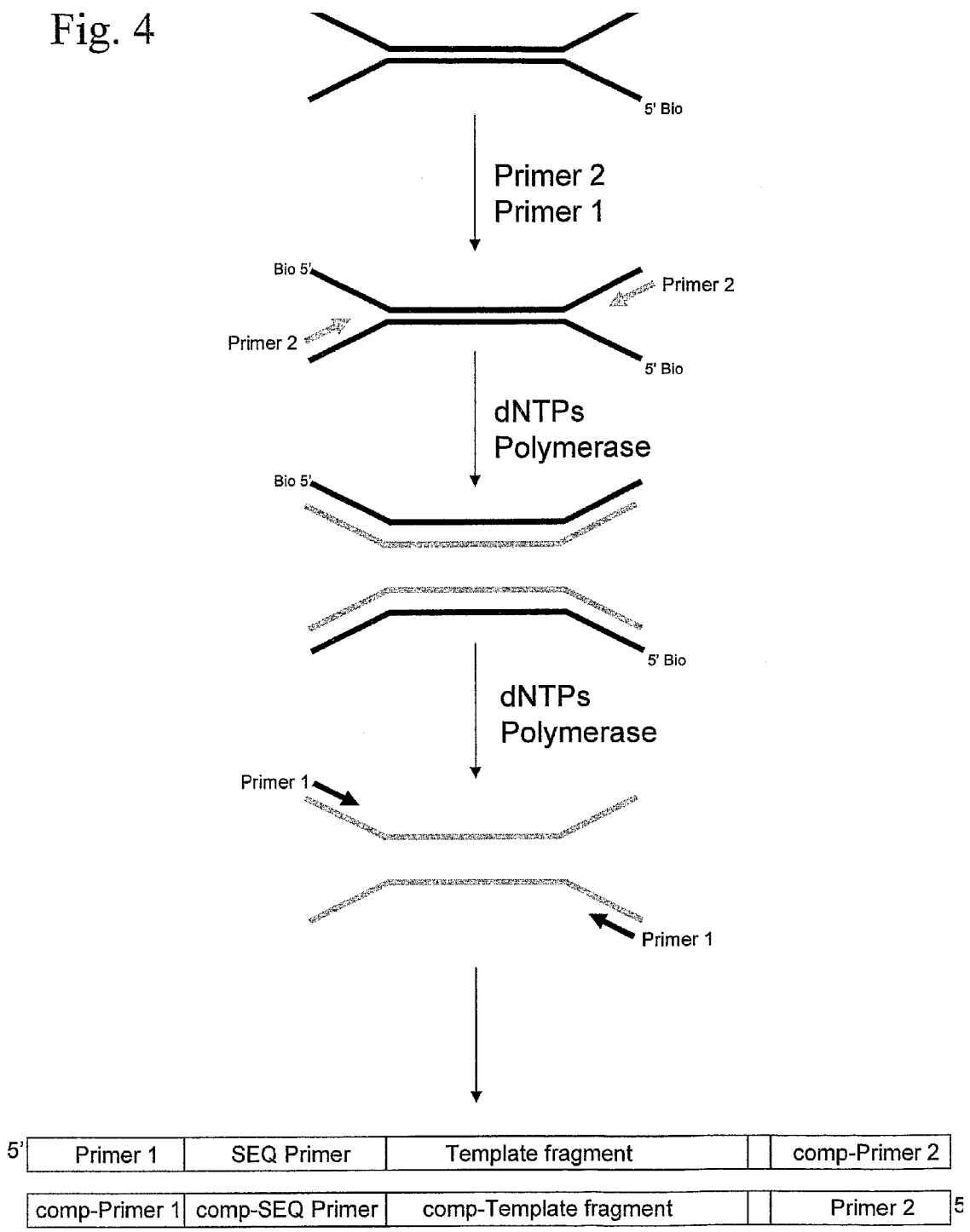
FIG. 4 illustrates a still further embodiment of the invention in which adapter-target constructs are subjected to PCR amplification to generate multiple double-stranded copies of each adapter-target construct. For simplicity PCR amplification illustrated for a single adapter-target construct.

In another embodiment of the invention, illustrated in FIG. 4, the initial primer extension reaction on the bead-immobilised adapter-target constructs with PRIMER 2 forms part of a standard (symmetric) PCR amplification with the PRIMER 2 and PRIMER 1 oligonucleotides. In this embodiment, multiple double-stranded copies of the bead-immobilised strands are generated in the supernatant of the bead suspension due to PCR thermocycling, hence a separate denaturation step is not necessary to recover the newly synthesised complementary copies of the bead-immobilised adapter-target strands; the copies can be purified from the supernatant by standard methods, known to those skilled in the art.

Figure 5:
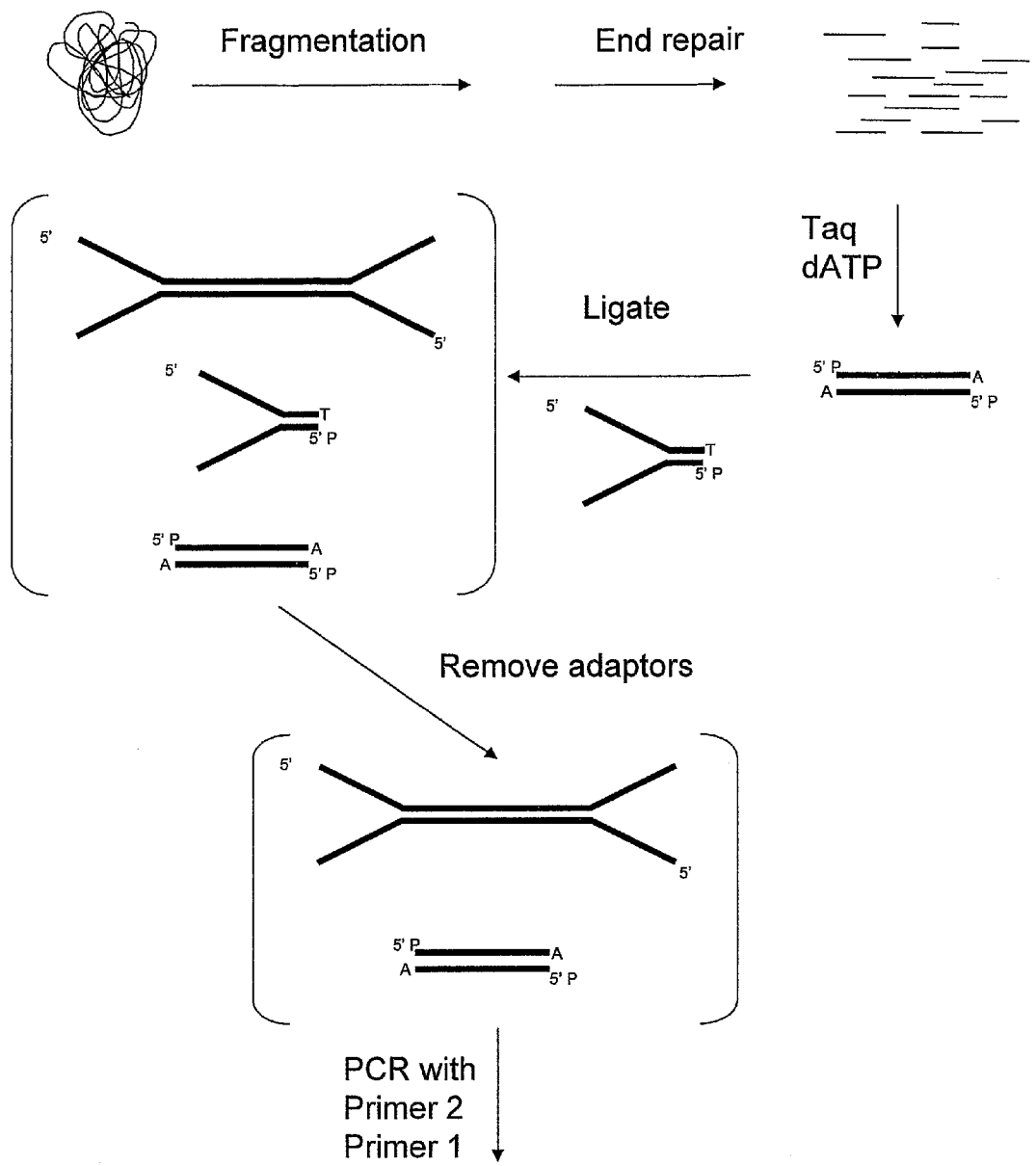
FIG. 5 illustrates an embodiment of the invention, depicting steps of fragmenting a complex sample such as genomic DNA to generate a plurality of target fragments, ligation of the target fragments to mismatched (forked) adapters to generate adapter-template constructs and subsequent removal of unbound adapters, wherein the adapters do not include a biotin group at the 5' end. The resulting adapter-target constructs may be subjected to PCR amplification to generate multiple double-stranded copies of each adapter-target construct. For simplicity the ligation steps are illustrated for a single adapter-target construct.

In another embodiment of the invention, illustrated in FIG. 5, the forked adapter does not contain a biotin group at the 5' end of the Oligo A strand. In this embodiment, fragmented DNA may be made blunt-ended by a number of methods know to those skilled in the art. In the preferred method, the ends of the fragmented are end repaired with T4 DNA polymerase and Klenow polymerase, and then phosphorylated with polynucleotide kinase enzyme. A single 'A' deoxynucleotide is then added to both 3' ends of the DNA molecules with Taq polymerase enzyme, producing a one-base 3' overhang that is complementary to the one-base 3"T' overhang on the double-stranded "ligatable" end of the forked adapter. A ligation reaction between the forked adapter and the DNA fragments is then performed, e.g. using T4 DNA ligase enzyme, which joins two copies of the adapter to each DNA template molecule, one at either end.

The products of the ligation reaction can be purified from unligated adapter by a number of means, including size-inclusion chromatography, preferably by electrophoresis through an agarose gel slab followed by excision of a portion of the agarose that contains the DNA greater in size that the size of the adapter. An aliquot of the purified DNA is then used in a PCR amplification with the PRIMER 2 and PRIMER 1 oligonucleotides (FIG. 5). The first PCR cycle will involve an initial primer extension reaction with primer 2 (not illustrated). The primers selectively amplify those template DNA molecules that have adapters ligated on both ends. The product of the reaction is a library of double-stranded template molecules, each of which comprise in order on one of the duplex strands: 5' PRIMER 2 sequence, target DNA, the complement of SEQ PRIMER sequence, then the complement of PRIMER 1 sequence. This library can then be used on a solid-phase PCR platform that contains immobilised PRIMER 1 and PRIMER 2 oligonucleotides.

Figure 6:
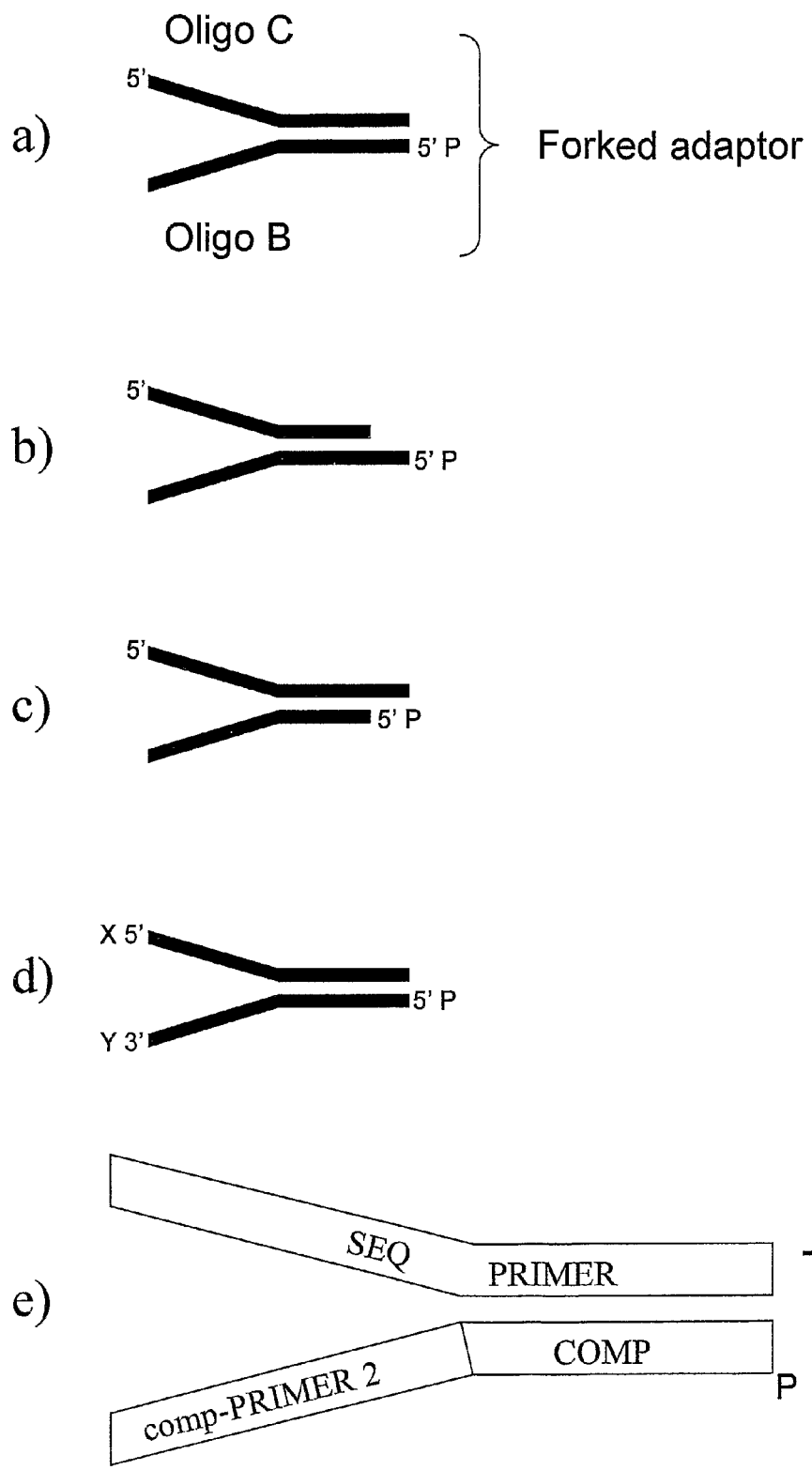
FIG. 6 illustrates further examples of forked mismatched adapters for use in the method of the invention, again depicting the permissible blunt or overhang formats at the "ligatable" end of the adapter.

FIG. 6 illustrates further examples of forked mismatched adapters for use in the method of the invention. In this embodiment the forked adapter is formed by annealing two single-stranded oligonucleotides, herein referred to as "oligo C" and "oligo B". The oligonucleotides are partially complementary such that the 3' end of oligo C is complementary to the 5' end of oligo B. The 5' end of oligo C and the 3' end of oligo B are not complementary to each other. When the two oligos are annealed the resulting structure is double-stranded at one end (double-stranded region) and single-stranded at the other end (unmatched region) (FIG. 6a). The double-stranded region of the forked adapter may be blunt-ended (FIG. 6d) or it may have an overhang. In the latter case, the overhang may be a 3' overhang (FIG. 6c) or a 5' overhang (FIG. 6b), and may comprise a single base or more than one base.

The 5' end of the double-stranded region of the forked adapter is phosphorylated i.e. the 5' end of 'oligo B' (FIG. 6a-d) to provide a "ligatable" end. The 5' end of oligo C may be biotinylated or bear another functionality (X) that enables it to be captured on a surface, such as a bead. The 3' end of oligo B may also be biotinylated or bear another functionality (Y) that enables it to be captured on a surface (FIG. 6d).

The phosphodiester bonds that comprise the back-bone of the oligonucleotides may be replaced with non-enzymatically cleavable bonds such as phosphorothioate bonds. Preferably only the last, or last and penultimate, phosphodiester bonds at both the 3' and 5' ends of the oligonucleotides will be substituted with phosphorothioate bonds. Oligo C consists of only one sequence: a sequence identical to that of a universal sequencing primer denoted "SEQ PRIMER" (or identical to part of the 3' end of the "SEQ PRIMER" sequence), plus an additional 'T' nucleotide on the 3' end. Oligo B consists of two sequences: a sequence at its 5' end that is complementary to only part of the 3' end of the SEQ PRIMER sequence in Oligo C, excluding the 'T' overhang of 'Oligo C', and a sequence at its 3' end which is complementary to that of a universal PCR amplification primer, herein referred to as the "comp-PRIMER 2" sequence, (FIG. 6e).

Figure 7A:
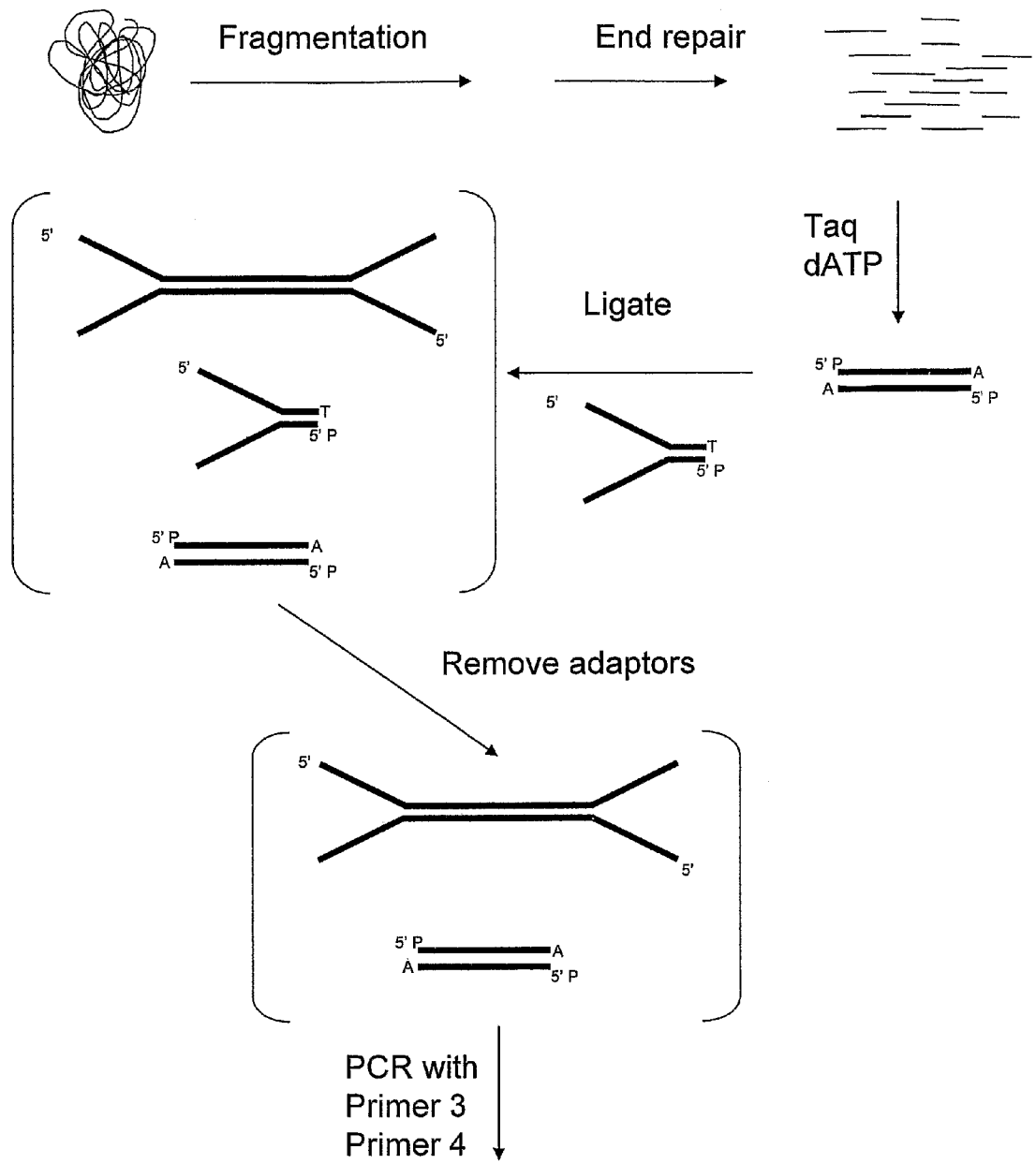

FIG. 7 illustrates a further embodiment of the invention based on use of the forked adapters illustrated in FIG. 6. In this embodiment, adapter-target constructs are prepared substantially as described above with reference to FIG. 5, except that the adapters illustrated in FIG. 6 are used (FIG. 7a).

An aliquot of the purified adapter-target constructs is used in a standard solution-phase PCR amplification with "tailed" primer oligonucleotides. Tailed primers are primers that only hybridize via their 3' end to a target sequence, leaving a 5' non-hybridised tail. The length and precise sequence of the non-hybridised tail is non-limiting, but may typically comprise from 10 to 50 nucleotides, more typically from 15 to 30 nucleotides. When used in amplifications by PCR, the initial round of PCR amplification (i.e. the first and second primer extension reactions) rely on binding of the 3' ends of the tailed primers to cognate primer-binding sequences in the adapter regions of the adapter-target constructs. The 5' non-hybridising tails derived from the tailed primers act as templates in subsequent PCR cycles and are therefore copied into the resultant double-stranded PCR products.

In the current embodiment, either one or both of the primers used in the amplification reaction can be "tailed" primers. In one embodiment, the primers used are denoted PRIMER 3 and PRIMER 4, where PRIMER 3 consists of a 5' tail sequence, and a 3' sequence that is complementary to the "comp PRIMER 2" sequence in the forked adapter; and PRIMER 4 consists of a 5' tail sequence, and a 3' sequence that is identical to the 5' end of the SEQ PRIMER sequence present in the unmatched region of the forked adapter. Following amplification by PCR, the tail sequences are incorporated into the copies of the adapter-target DNA construct.

In one embodiment of the invention, the tail sequences on PRIMER 3 and PRIMER 4 are non-identical sequences. The tail sequence of PRIMER 3 and the tail sequence of PRIMER 4 can then be used to form the sequence of surface-immobilised primers to be used on a solid-phase DNA amplification platform (FIG. 7b).

In another embodiment of the invention, the tail sequences on PRIMER 3 and PRIMER 4 are identical sequences. The products of the solution-phase PCR will thus have the same sequence at their ends: the common tail sequence of PRIMER 3 and PRIMER 4. This common tail sequence can then be used to form the sequence of a single surface-immobilised primer on a solid-phase DNA amplification platform. Surface amplification of the library of templates may thus be performed using a single PCR primer immobilised on the surface.

Figure 8:
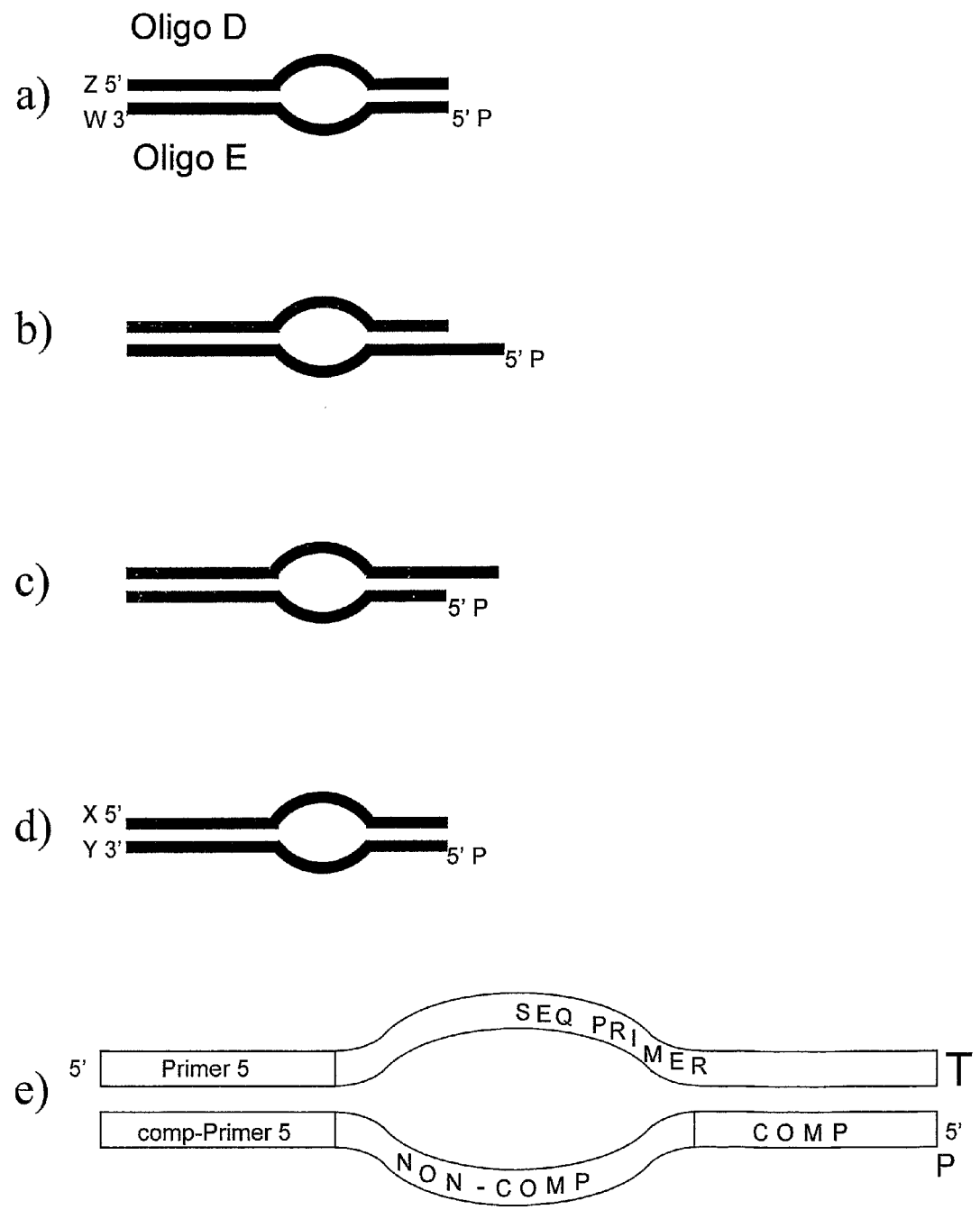
FIG. 8 illustrates alternative embodiments of mismatched adapters for use in the method of the invention. P represents a terminal phosphate group; X and Y represent surface capture functionalities; X and Z represent modifications to prevent ligation.

FIG. 8 illustrates alternative embodiments of mismatched adapters for use in the method of the invention. These "modified" forked adapters may be designed to enable solid-phase amplification of templates using a single surface bound primer. The adapter is formed by annealing two single-stranded oligonucleotides, herein referred to as "oligo D" and "oligo E". The oligonucleotides are partially complementary such that the 3' end of oligo D is complementary to the 5' end of oligo E, and the 5' end of oligo D is complementary to the 3' end of oligo E, however the central portions of oligo D and oligo E are non-complementary. When the oligo D and oligo E are annealed the resulting structure is double stranded at both ends (double-stranded regions) and single stranded in the middle (unmatched region) and is referred to herein as the "modified Forked adapter" (FIG. 8a).

One end of the modified forked adapter is modified to prevent ligation of a DNA molecule to this end. Such modifications are known to those skilled in the art and may include, for example, the presence of a 5' or 3' overhang. The other "ligatable" end may be blunt-ended (FIG. 8d) or may have an overhang. In the latter case, the overhang may be a 3' overhang (FIG. 8c) or a 5' overhang (FIG. 8b), and may comprise a single base or more than one base. The 5' strand of the ligatable end is phosphorylated i.e. the 5' end of oligo E (FIG. 8a-d). The 5' end of oligo D may be biotinylated or bear another functionality that enables it to be captured on a surface, such as a bead. The 3' end of oligo E may be biotinylated or bear another functionality that enables it to be captured on a surface (FIG. 8d). The modifications to prevent ligation (Z,W) may be the same as or different to the surface capture functionalities (X,Y).

The phosphodiester bonds that comprise the back-bone of the oligonucleotides may be replaced with non-enzymatically cleavable bonds such as phosphorothioate bonds. Preferably only the last, or last and penultimate, phosphodiester bonds at both the 3' and 5' ends of the oligonucleotides will be substituted with phosphorothioate bonds.

In the preferred embodiment of the invention, oligo E is phosphorylated at its 5' end and the 3' end of oligo D contains a single base 3' overhang comprising a "T" nucleotide. Oligo D consists of two sequences: a sequence at its 5' end which is identical to that of a universal PCR amplification primer, referred to herein as "PRIMER 5" sequence, next to a sequence identical to that of a universal sequencing primer denoted "SEQ PRIMER" sequence plus the additional "T" nucleotide on the 3' end. Oligo E consists of three sequences: a sequence at its 5' end that is complementary to only part of the 3' end of the SEQ PRIMER sequence in Oligo D, excluding the 'T' overhang of Oligo D, a central sequence non-complementary to any part of Oligo D, and a 3' end that is complementary to the "PRIMER 5" sequence of Oligo D (FIG. 8e).

Figure 9A:
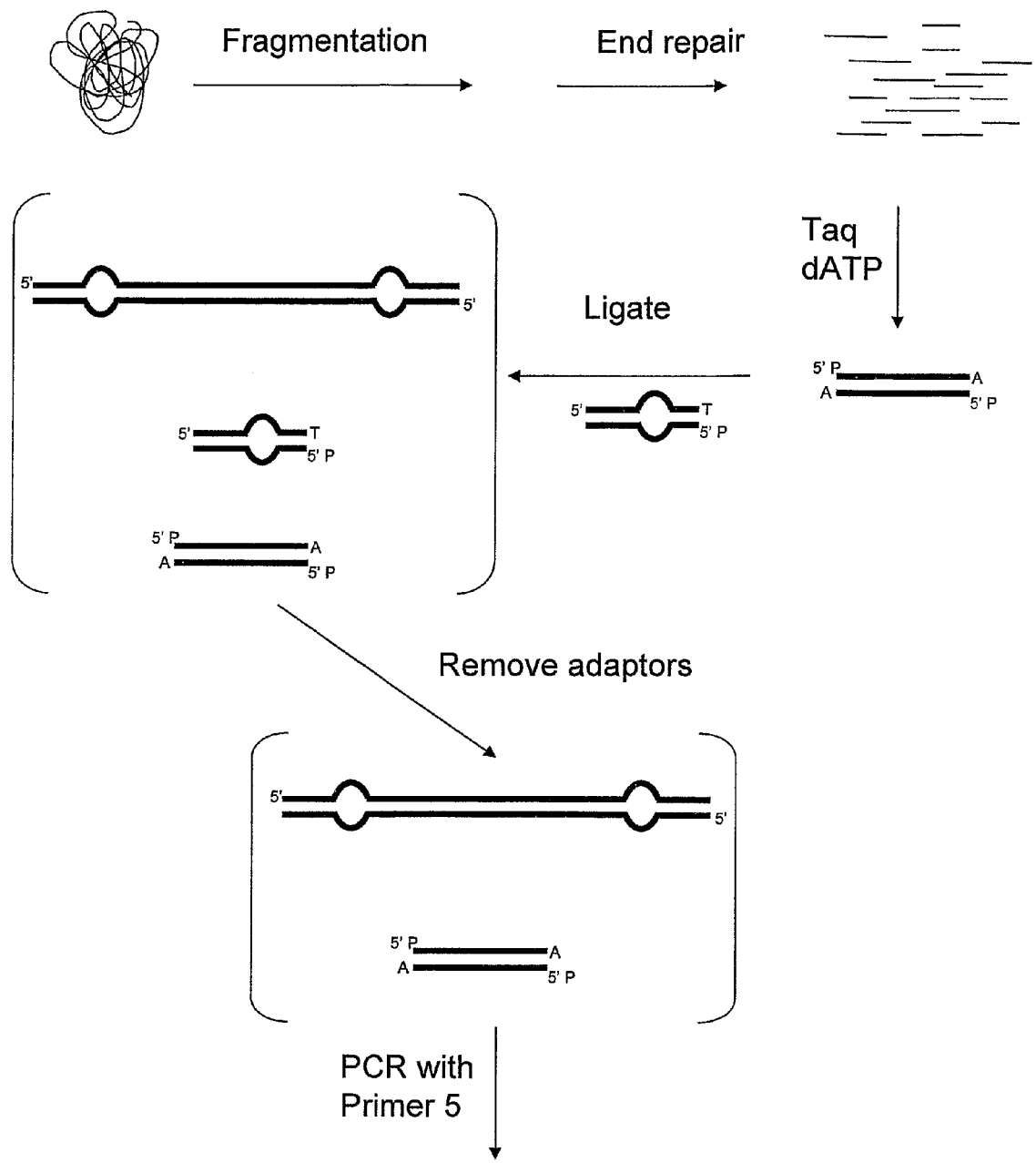
FIG. 9a illustrates a still further embodiment of the invention based on use of the alternative adapters illustrated in FIG. 8.
Figure 9B:
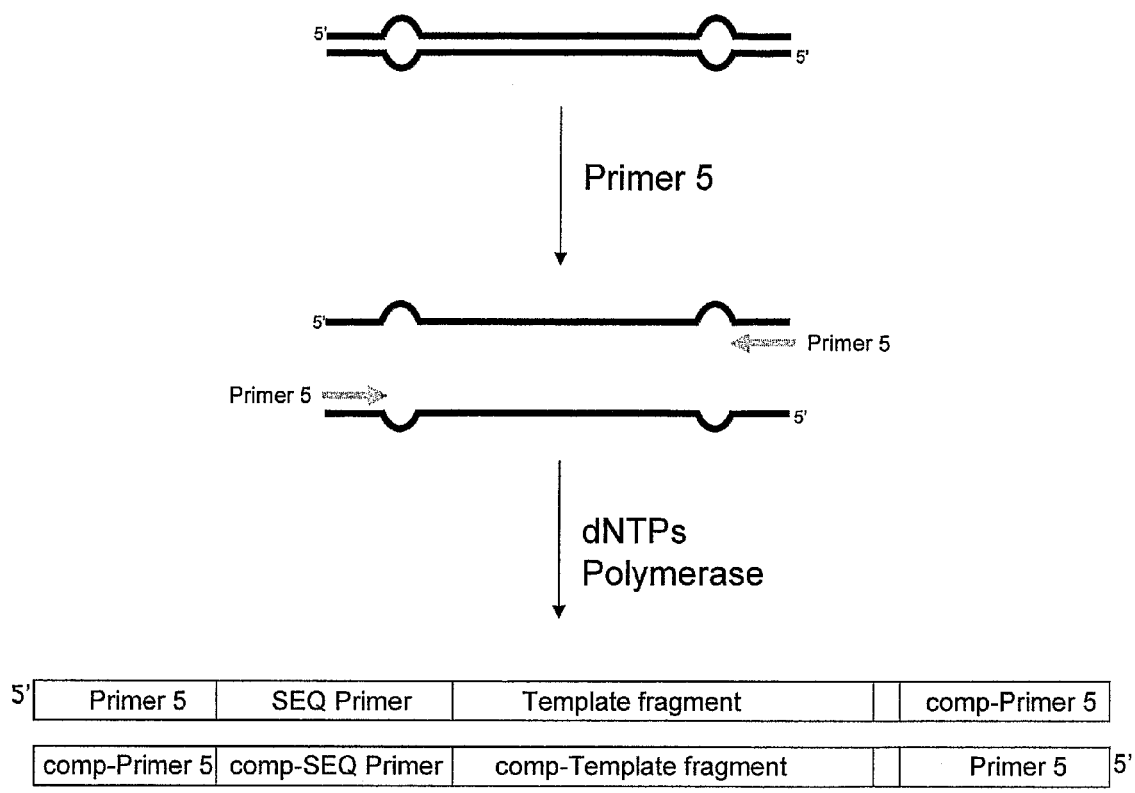
FIG. 9(b) depicts annealing of identical amplification primers to a double-stranded region of the adapter on each strand of the adapter-target construct. The adapter-target constructs can be amplified by PCR using this single primer species. For simplicity the ligation steps and primer annealing are illustrated for a single adapter-target construct.

FIG. 9 illustrates a still further embodiment of the invention based on use of the alternative adapters illustrated in FIG. 8. In this embodiment adapter-target constructs may be prepared substantially as described above in relation to FIG. 5, except that the modified forked adapters illustrated in FIG. 8 are used. An aliquot of the purified adapter-target constructs is used in a solution-phase PCR amplification using PRIMER 5 oligonucleotide to selectively amplify those ligation products that have the modified adapter on both ends (FIG. 9b). The product of the solution-phase PCR can then be purified and amplified on a solid-phase PCR platform with a single immobilised primer, e.g. PRIMER 5. Inclusion of the mismatch sequence in oligo E ensures that all products of this solid-phase amplification will contain common sequencing primer binding sequences on one strand only, enabling sequencing using a universal sequencing primer which anneals to this common sequence.

Use of the Template Library

Template libraries prepared according to the method of the invention may be used in essentially any method of nucleic acid analysis which requires further amplification of the templates and/or sequencing of the templates or amplification products thereof. Exemplary uses of the template libraries include, but are not limited to, providing templates for whole genome amplification and also solid-phase PCR amplification (of either monotemplate or complex template libraries). A particularly preferred use is in whole-genome amplification carried out on a solid-support.

Whole-Genome Amplification

Template libraries prepared according to the method of the invention starting from a complex mixture of genomic DNA fragments representing a whole or substantially whole genome provide suitable templates for so-called "whole-genome" amplification. The term "whole-genome amplification" refers to a nucleic acid amplification reaction (e.g. PCR) in which the template to be amplified comprises a complex mixture of nucleic acid fragments representative of a whole (or substantially whole genome).

Solid-Phase Amplification

Once formed, the library of templates prepared according to the methods described above can be used for solid-phase nucleic acid amplification.

Thus, in further aspects the invention provides a method of solid-phase nucleic acid amplification of template polynucleotide molecules which comprises:

preparing a library of template polynucleotide molecules which have common sequences at their 5' and 3' ends using a method according to the first aspect of the invention described herein and carrying out a solid-phase nucleic acid amplification reaction wherein said template polynucleotide molecules are amplified.

The term "solid-phase amplification" as used herein refers to any nucleic acid amplification reaction carried out on or in association with a solid support such that all or a portion of the amplified products are immobilised on the solid support as they are formed. In particular, the term encompasses solid-phase polymerase chain reaction (solid-phase PCR), which is a reaction analogous to standard solution phase PCR, except that one or both of the forward and reverse amplification primers is/are immobilised on the solid support.

Although the invention encompasses "solid-phase" amplification methods in which only one amplification primer is immobilised (the other primer usually being present in free solution), it is preferred for the solid support to be provided with both the forward and the reverse primers immobilised. In practice, there will be a "plurality" of identical forward primers and/or a "plurality" of identical reverse primers immobilised on the solid support, since the PCR process requires an excess of primers to sustain amplification. References herein to forward and reverse primers are to be interpreted accordingly as encompassing a "plurality" of such primers unless the context indicates otherwise.

As will be appreciated by the skilled reader, any given PCR reaction requires at least one type of forward primer and at least one type of reverse primer specific for the template to be amplified. However, in certain embodiments the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other embodiments may use forward and reverse primers which contain identical template-specific sequences but which differ in some other structural features. For example one type of primer may contain a non-nucleotide modification which is not present in the other.

In other embodiments of the invention the forward and reverse primers may contain template-specific portions of different sequence.

In all embodiments of the invention, amplification primers for solid-phase PCR are preferably immobilised by covalent attachment to the solid support at or near the 5' end of the primer, leaving the template-specific portion of the primer free for annealing to it's cognate template and the 3' hydroxyl group free for primer extension. Any suitable covalent attachment means known in the art may be used for this purpose. The chosen attachment chemistry will depend on the nature of the solid support, and any derivatisation or functionalisation applied to it. The primer itself may include a moiety, which may be a non-nucleotide chemical modification, to facilitate attachment. In one particularly preferred embodiment the primer may include a sulphur-containing nucleophile, such as phosphorothioate or thiophosphate, at the 5' end. In the case of solid-supported polyacrylamide hydrogels (as described below), this nucleophile will bind to a "C" group present in the hydrogel. The most preferred means of attaching primers and templates to a solid support is via 5' phosphorothioate attachment to a hydrogel comprised of polymerised acrylamide and N-(5-bromoacetamidylpentyl) acrylamide (BRAPA).

It is preferred to use the library of templates prepared according to the first aspect of the invention to prepare clustered arrays of nucleic acid colonies, analogous to those described in WO 00/18957 and WO 98/44151, by solid-phase PCR amplification. The terms "cluster" and "colony" are used interchangeably herein to refer to a discrete site on a solid support comprised of a plurality of identical immobilised nucleic acid strands and a plurality of identical immobilised complementary nucleic acid strands. The term "clustered array" refers to an array formed from such clusters or colonies. In this context the term "array" is not to be understood as requiring an ordered arrangement of clusters.

Use in Sequencing/Methods of Sequencing

The invention also encompasses methods of sequencing amplified nucleic acids generated by whole genome or solid-phase amplification. Thus, the invention provides a method of nucleic acid sequencing comprising amplifying a library of nucleic acid templates using whole genome or solid-phase amplification as described above and carrying out a nucleic acid sequencing reaction to determine the sequence of the whole or a part of at least one amplified nucleic acid strand produced in the whole genome or solid-phase amplification reaction.

Sequencing can be carried out using any suitable "sequencing-by-synthesis" technique, wherein nucleotides are added successively to a free 3' hydroxyl group, resulting in synthesis of a polynucleotide chain in the 5' to 3' direction. The nature of the nucleotide added is preferably determined after each nucleotide addition.

The initiation point for the sequencing reaction may be provided by annealing of a sequencing primer to a product of the whole genome or solid-phase amplification reaction. In this connection, one or both of the adapters added during formation of the template library may include a nucleotide sequence which permits annealing of a sequencing primer to amplified products derived by whole genome or solid-phase amplification of the template library.

The products of solid-phase amplification reactions wherein both forward and reverse amplification primers are covalently immobilised on the solid surface are so-called "bridged" structures formed by annealing of pairs of Immobilised polynucleotide strands and immobilised complementary strands, both strands being attached to the solid support at the 5' end. Arrays comprised of such bridged structures provide inefficient templates for nucleic acid sequencing, since hybridisation of a conventional sequencing primer to one of the immobilised strands is not favoured compared to annealing of this strand to its immobilised complementary strand under standard conditions for hybridisation.

In order to provide more suitable templates for nucleic acid sequencing it is preferred to remove substantially all or at least a portion of one of the immobilised strands in the "bridged" structure in order to generate a template which is at least partially single-stranded. The portion of the template which is single-stranded will thus be available for hybridisation to a sequencing primer. The process of removing all or a portion of one immobilised strand in a "bridged" double-stranded nucleic acid structure may be referred to herein as "linearisation".

Bridged template structures may be linearised by cleavage of one or both strands with a restriction endonuclease or by cleavage of one strand with a nicking endonuclease. Other methods of cleavage can be used as an alternative to restriction enzymes or nicking enzymes, including inter alfa chemical cleavage (e.g. cleavage of a diol linkage with periodate), cleavage of abasic sites by cleavage with endonuclease, or by exposure to heat or alkali, cleavage of ribonucleotides incorporated into amplification products otherwise comprised of deoxyribonucleotides, photochemical cleavage or cleavage of a peptide linker.

It will be appreciated that a linearization step may not be essential if the solid-phase amplification reaction is performed with only one primer covalently immobilised and the other in free solution.

In order to generate a linearised template suitable for sequencing it is necessary to remove "unequal" amounts of the complementary strands in the bridged structure formed by amplification so as to leave behind a linearised template for sequencing which is fully or partially single stranded. Most preferably one strand of the bridged structure is substantially or completely removed.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions will be apparent to the skilled reader with reference to standard molecular biology protocols (Sambrook et al., 2001, *Molecular Cloning, A Laboratory Manual,* 3rd Ed, Cold Spring Harbor Laboratory Press, Cold Spring Harbor Laboratory Press, NY; Current Protocols, eds Ausubel et al.).

Denaturation (and subsequent re-annealing of the cleaved strands) results in the production of a sequencing template which is partially or substantially single-stranded. A sequencing reaction may then be initiated by hybridisation of a sequencing primer to the single-stranded portion of the template.

Thus, the nucleic acid sequencing reaction may comprise hybridising a sequencing primer to a single-stranded region of a linearised amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

One preferred sequencing method which can be used in accordance with the invention relies on the use of modified nucleotides that can act as chain terminators. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

The modified nucleotides may carry a label to facilitate their detection. Preferably this is a fluorescent label. Each nucleotide type may carry a different fluorescent label. However the detectable label need not be a fluorescent label. Any label can be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means.

The invention is not intended to be limited to use of the sequencing method outlined above, as essentially any sequencing methodology which relies on successive incorporation of nucleotides into a polynucleotide chain can be used. Suitable alternative techniques include, for example, Pyrosequencing™, FISSEQ (fluorescent in situ sequencing), MPSS (massively parallel signature sequencing) and sequencing by ligation-based methods.

The target polynucleotide to be sequenced using the method of the invention may be any polynucleotide that it is desired to sequence. Using the template library preparation method described in detail herein it is possible to prepare template libraries starting from essentially any double or single-stranded target polynucleotide of known, unknown or partially known sequence. With the use of clustered arrays prepared by solid-phase amplification it is possible to sequence multiple targets of the same or different sequence in parallel.

Kits

The invention also relates to kits for use in preparing libraries of template polynucleotides using the method of the first aspect of the invention.

Preferred embodiments of the kit comprise at least a supply of a mismatched adapter as defined herein, plus a supply of at least one amplification primer which is capable of annealing to the mismatched adapter and priming synthesis of an extension product, which extension product would include any target sequence ligated to the adapter when the adapter is in use.

The preferred features of the "mismatch" adapters for inclusion in the kit are as described elsewhere herein in relation to other aspects of the invention. The structure and properties of amplification primers will be well known to those skilled in the art. Suitable primers of appropriate nucleotide sequence for use with the adapters included in the kit can be readily prepared using standard automated nucleic acid synthesis equipment and reagents in routine use in the art. The kit may include as supply of one single type of primer or separate supplies (or even a mixture) of two different primers, for example a pair of PCR primers suitable for PCR amplification of templates modified with the mismatched adapter in solution phase and/or on a suitable solid support (i.e. solid-phase PCR).

In one embodiment the kit may include supplies of different primer-pairs for use in solution phase and solid phase PCR. In this context the "different" primer-pairs may be of substantially identical nucleotide sequence but differ with respect to some other feature or modification, such as for example surface-capture moieties, etc. In other embodiments the kit may include a supply of primers for use in an initial primer extension reaction and a different primer-pair (or pairs) for solution and/or solid phase PCR amplification.

Adapters and/or primers may be supplied in the kits ready for use, or more preferably as concentrates-requiring dilution before use, or even in a lyophilised or dried form requiring reconstitution prior to use. If required, the kits may further include a supply of a suitable diluent for dilution or reconstitution of the primers. Optionally, the kits may further comprise supplies of reagents, buffers, enzymes, dNTPs etc for use in carrying out PCR amplification. Suitable (but non-limiting) examples of such reagents are as described in the Materials and Methods sections of the accompanying Examples. Further components which may optionally be supplied in the kit include "universal" sequencing primers suitable for sequencing templates prepared using the mismatched adapters and primers, The invention will be further understood with reference to the following non-limiting experimental example:

EXAMPLE

Experimental Overview

The following experimental details describe the complete exposition of one embodiment of the invention as described above. The DNA source used is purified Human cell line DNA supplied by the Coriell Cell Repositories, Camden, N.J. 08103 USA, catalog no. NA07055. The DNA is first prepared for ligation to forked adapters by: fragmentation of the DNA by nebulisation, end repair of the DNA ends to make them blunt-ended and phosphorylation, then the addition of a single 'A' nucleotide onto the 3' ends of the human DNA fragments. The ligation reaction is performed with the prepared fragmented DNA and adapters pre-formed by annealing 'Oligo A' and 'Oligo B' (sequences given below). The product of the reaction is isolated/purified from unligated adapter by gel electrophoresis. Finally, the product of the ligation reaction is subject to cycles of PCR to selectively amplify ligated product that contains adapter at both ends of the fragments.

Materials and Methods

Nebulization

Materials:

| | |
|---|---|
| Human genomic DNA (1 mg/ml) | Coriell NA07055 |
| Buffer (glycerol 53.1 ml, water 42.1 ml, 1M TrisHCl pH7.5 3.7 ml, 0.5M EDTA 1.1 ml) | |
| Nebulizer | Invitrogen (#K7025-05) |
| Qiagen columns | PCR purification kit (#28104) |

Mix: 25 µl (5 micrograms) of DNA
725 µl Buffer

Procedure:

Chilled DNA solution was fragmented in the nebulizer on ice for 5 to 6 minutes under at least 32 psi of pressure. The recovered volume (usually somewhere between 400 and 600 µl) was split into 3 aliquots and purified with a Qiagen PCR-purification kit, but using only one column, and finally eluted in 30 µl of EB (Qiagen).

End-Repair

Materials:

| | |
|---|---|
| T4 DNA Polymerase | NEB #M0203S |
| 10xNEB 2 buffer | NEB #M7002S |
| 100x BSA | NEB #M9001S |
| dNTPs mix (10 mM each) | NEB #N0447S |
| E. coli DNA Pol I large fragment (Klenow, NEB #M0210S) | |
| T4 polynucleotide kinase | NEB #M0201S |
| T4 PNK buffer | NEB #M0201S |
| 100 mM ATP | |
| Qiagen columns | PCR purification kit (#28104) |

End repair mix was assembled as follows:

| | |
|---|---|
| DNA | 30 µl |
| Water | 12 µl |
| 10xNEB2 | 5 µl |
| 100xBSA | 0.5 µl |
| 10 mM dNTPs | 2 µl |
| T4 DNA pol (3 U/µl) | 5 µl |
| | 50 µl total |

The reaction was incubated for 15 min at room temperature, then 1 µl of E. coli DNA Pol I large fragment (Klenow) added and the reaction incubated for a further 15 min at room temperature. The DNA was purified from enzymes, buffer, etc by loading the reaction mix on a Qiagen column, finally eluting in 30 µl EB. The 5' ends of the DNA were then phosphorylated using polynucleotide kinase as follows:

| | |
|---|---|
| DNA | 30 µl |
| Water | 9.5 µl |
| 10xPNK buffer | 5 µl |
| 100 mM ATP | 0.5 µl |
| T4 PNK (10 U/µl) | 5 µl |
| | 50 µl total |

The reaction was incubated for 30 min at 37° C., then heat inactivated at 65° C. for 20 min. DNA was then purified from enzymes, buffer, etc by loading the reaction mix on a Qiagen column, finally eluting in 30 µl EB. Three separate tubes were pooled to give 90 µl total.

A-Tailing Reaction

Materials:

| | |
|---|---|
| Taq DNA polymerase | NEB #M0267L |
| 10x thermopol buffer | NEB #B9004S |
| 1 mM dATP | Amersham-Pharmacia #272050 |
| Qiagen MinElute column | PCR purification kit (#28004) |

The following reaction mix was assembled:

| | |
|---|---|
| DNA | 30 µl |
| 10x thermopol buffer | 5 µl |
| 1 mM dATP | 10 µl |
| Taq pol (5 U/µl) | 3 µl |
| | ~50 µl total |

The reaction was incubated for 30 min at 70° C., then the DNA purified from enzymes, buffer, etc by loading the reaction mix on a Qiagen MinElute column, finally eluting in 10 µl EB.

Anneal Forked Adapter

Materials:

| |
|---|
| 'Oligo A' and 'Oligo B' |
| 50 mM Tris/50 mM NaCl pH7 |
| PCR machine |

| | |
|---|---|
| 100 µM Oligo A | 20 µl |
| 100 µm Oligo B | 20 µl |

| | |
|---|---|
| Tris/NaCl | 10 µl |
| | 50 µl at 40 µM duplex in 10 mM Tris/10 mM NaCl pH 7.5 |

Oligo A: 5'ACACTCTTTCCCTACACGACGCTCTTCCGATCxT (x = phosphorothioate bond) (SEQ ID NO: 1)
Oligo B: 5'Phosphate-GATCGGAAGAGCTCGTATGCCGTCTTCTGCTTG (SEQ ID NO: 2)

The adapter strands were annealed in a PCR machine programmed as follows:
Ramp at 0.5° C./sec to 97.5° C.
Hold at 97.5° C. for 150 sec
Then a step of 97.5° C. for 2 sec with a temperature drop of 0.1° C./cycle for 775 cycles Ligation Reaction
Materials:

| | |
|---|---|
| 40 µM forked adapter | |
| A-tailed genomic DNA | |
| Quick Ligase | NEB #M2200L |
| Quick Ligase 2x buffer | NEB #M2200L |
| PCR machine | |
| Qiagen columns | PCR purification kit (#28104) |

Reaction mix was assembled as follows:

| | |
|---|---|
| DNA | 10 µl |
| 2x buffer | 25 µl |
| 40 µM adapter | 10 µl |
| Quick Ligase | 5 µl |
| | ~50 µl total |

The reaction was incubated for 20 min at room temperature then the DNA purified from enzymes, buffer, etc by loading the reaction mix on a Qiagen column, finally eluting in 30 µl EB.

Gel Purification
Materials:

| | |
|---|---|
| Agarose | Biorad #161-3101 |
| 100 base pair ladder | NEB #N3231L |
| TAE | |
| Loading buffer (50 mM Tris pH 8, 40 mM EDTA, 40% w/v sucrose) | |
| Ethidium bromide | |
| Gel trays and tank. Electrophoresis unit | |

The entire sample from the purified ligation reaction was loaded into one lane of a 2% agarose gel containing ethidium bromide and run at 120V for 50 min. The gel was then viewed on a 'White-light' box and fragments from above 300 bp to at least 750 bp excised and purified with a Qiagen Gel purification kit, eluting in 30 µl EB. For large gel slices two minElute columns were used, eluting each in 15 µl EB and pool.

PCR Amplification
Materials:

Ligated DNA

PRIMER 1:
AATGATACGGCGACCACCGAGATCTACACTCTTTCCCTACACGA
(SEQ ID NO: 3)

PRIMER 2: CAAGCAGAAGACGGCATACGA
(SEQ ID NO: 4)

2x Jump Start RedTaq PCR mix     Sigma #P0982

PCR machine

Qiagen MinElute columns     Qiagen(#28004)

The purified ligated DNA was diluted 25 fold, then a PCR reaction mix prepared as follows:

| | |
|---|---|
| DNA | 1 µl |
| 2x Jump Start RedTaq mix | 25 µl |
| 100 µM Primer 1 | 0.5 µl |
| 100 µM Primer 2 | 0.5 µl |
| Water | 23 µl |
| | ~50 µl total |

Thermocycling was carried out in a PCR machine under the following conditions:

2 min @ 94° C.
[45 sec@ 94° C., 45 sec @ 65° C., 2 min @ 70° C.] 16 cycles
5 min @ 70° C.
Hold @ 4° C.

PCR products were purified from enzymes, buffer, etc on a Qiagen MinElute column, eluting in 10 µl EB. The resulting DNA library is ready for amplification on a surface PCR platform.

Validation of Library

1 µl of the DNA library was cloned into a plasmid vector and plated out on agar. 19 colonies were picked, miniprepped and the cloned inserts sequenced by conventional Sanger sequencing. The sequence data obtained was as follows:

```
Clone 1 (SEQ ID NO: 5)
TGATACGGCGACCACCGAGATCTACACTCTTTCCCTACACGACGCTCTTCCGATCTGTGG

GGACCGTCCTGTGCATTGTAGGGTGTTCAACAGCATCCCTGACCTCCACCTACAAGATGC

CAGTAGCGAATCCCCTCAGCCCTCATCTCCTTGCCATAGTTGTGTCAACCAAAATCATCT

CCACACATTGTTAGATGTTTACTGGGAGGCAGACTCACTCCCACTTGAGAACCACTGTAC

TAGAAATATCACCAAGAGAATGAGATCGGAAGAGCTCGTATGCCGTCTTCTGCTTG

Clone 2 (SEQ ID NO: 6)
AATGATACGGCGACCACCGAGATCTACACTCTTTCCCTACACGACGCTCTTCCGATCTGT

GGGCTTTGTTCTTTGAGAGGTTGCAGTCAACATGATTCTTTAAGACCAGAACCCTGCACA
```

-continued
```
CTTCTTGGGCTGTATTTCTTACATTCCTTTTCTATTTTAACCATATCCCATCTTACCTAC

TTCCAGCATAGTGGTCATATTTAATTTTTACAAAACCATTTTGCCACTTGCTGCCAACTA

TGTTCTTTATAAAGCAGACTTTGAGATGGAGGCTAGTGTTCAGAGGGGATGCTTAGGAGA

ACTTTGGAGATTAATACTTATGGCAGGTAAGGGAAGGAAGCAGGATTAGACAGAAATATT

GAACTGTGATACAAAGTCAGCAAAGACTTTAGTCAATAGATCGGAAGAGCTCGTATGCCG

TCTTCTGCTTG

Clone 3 (SEQ ID NO: 7)
AATGATACGGCGACCACCGAGATCTACACTCTTTCCCTACACGACGCTCTTCCGATCTTT

CGATTCCCTTCAATGATTATTCCATTCGAGTACATTCGATGATTCCATTCGATTCTATAT

GATGATGATTGCATTCGAGTCCGTGTATTATTCCATTCCATTCCATTAGATGATTCCATT

CGAGTCCATTCGATGATTCTCTTCGATTCCGTTCGATAATTACGCTTGATTCCGTTTGAT

GTTGATTCCATTCGAGTCCATTCAATGTTAATTCCATTCGATTCTAAGCGATGATTCCAT

TCCTTTCCATTAGAAGATGATTCCATTCGAGACCATTCGATGATTGCATTCAACTCATTC

GATGACGATTCCATTCAATTCTGTTCAATGATTCCATTAGATTCCATTTGATGATGAGTC

CATTCGATTCCATTTGATGATGATTCCATGCGATTCCATTAGATGATGACCCCTTTCATT

TCCAAGATCGGAAGAGCTCGTATGCCGTCTTCTGCTTG

Clone 4 (SEQ ID NO: 8)
AATGATACGGCGACCACCGAGATCTACACTCTTTCCCTACACGACGCTCTTCCGATCTTT

AAATGCTAGGCATATTGTGTACCCCACATTGGTTTGTAGCCAGCTCTATGTCATAGGGCC

CTTACCCTTTACCTATTTATTGTTAGTATAATGTCCATAAACAAGCCAATGGCTCAGCAT

GAACTGATGCTAAAGAAAGCTCATGCCTGAGTGATAAATTAAGTGACCTCAGCTATTTCT

CTTCAGTGTTGTGAAAGTTATTTTTAACAGTAGGTTTCCTGGTAGATTCTCTAACCACTC

GGTATTTCACATGGCCCAACTTGGTTAACTCGACTGGTTACGGCAAATGCTGAAGATCGG

AAGAGCTCGTATGCCGTCTTCTGCTTG

Clone 5 (SEQ ID NO: 9)
AATGATACGGCGACCACCGAGATCTACACTCTTTCCCTACACGAAGCTCTTCCGATCTTA

AGGAAGTTAGGTAGATAATTTTTGTTTAGGCCATATAGCTTTGATTTTCTGATAACAATT

TTATAAACTTAGAAATTTTCATGTAAGATACAGGAATACTGGAAGCAAAAAAAGAAGGT

GCTTTAACCTTAGGGATTGAAAAAATAGTAATTTAGGTTGAAAATGCTGCTTGAAAGTTA

ATGCTGATAGCATTACTACACATGATGATTTTTCTGGAAGGAAAGCTTTATCTGGGCCT

TCAATTTAGGAATTTTTCTCTTTGGTTTTTAAAAGCTGCCATATTCACTTGAGCTTCATG

GGAAAGATGCAAATAACTAAAACAAATGAACAAAACCATGTTGAGGTCAGGAACTTATT

TCAAGAAAGCAAGTTCTAGGTTTTCTTTTAAAGTGACAGTAGAGCCTTAGGCCTCAAACC

ATCTACAACCATGTTAACAGTAAGATCGGAAGAGCTCGTATGCCGTCTTCTGCTTG

Clone 6 (SEQ ID NO: 10)
AATGATACGGCGACCACCGAGATCTACACTCTTTCCCTACACGACGCTCTTCAGATCTTC

CTGCCTCAGCCTCCCGAGTAGTTGGGATTGCAGGCATGTGCCACCATGCCCTGCTAATTT

TTGTATTTTAACTAAAGGAGGGGTTTTGCCATGTTGGCCAGGCTGGTCTTGAATGCCTG

ACCTCAGGTGATCCGCCCACCTCAGCCTCCCAGTGCTGGGATTACAGGTGTGAGCCACTG

CGCCCAGCTGAGGGTAACTATTTTTAATGTGGCTGATGAATGTAACTATCCTGTCCCATG

TCTCTGTCCCCAGCTGCAGAGCCCTCGTCGAGATCGGAAGAGCTCGTATGCCGTCTTCTG

CTTG
```

Clone 7 (SEQ ID NO: 11)
AATGATACGGCGACCACCGAGATCTACACTCTTTCCCTACACGACGCTCTTCCGATCTAA

GGTTTAAATTTTCTATATAGCCTGAAAAGTTTGAATGTTTAATTCAAACTAATTTATTGA

GCAATGGCATTTAAGAAAATGGAAAGATACAAAGGGACTTTCATCAGATGATAAGTGGAT

AAGAGAGAAAAATGCAGACAGATGAGCCAGAGTTGTGTAAAAGCTGGGAGGCTAGCAGGG

CCTTGTAGATAGCCAAGCTGACTGGGGAACAGAGATAAATGGGAGCAGAGATCAGAAAGT

TCATCCTTACCCTGCTGCCCGTGGTGAAAGGAGACTTGCAAGATCGGAAGAGCTCGTATG

CCGTCTTCTGCTTG

Clone 8 (SEQ ID NO: 12)
AATGATACGGCGACCACCGAGATCTACACTCTTTCCCTACACGACGCTCTTCCGATCTAA

GGAATCTTTATTTTCTACATTTGAGTTTGGAAAACTGAGCTAGCACATCTAAATCCATCT

AATTTTGGTCATTGGTTTTAACAAGTTCATCTTATTTTTTTAAACATCTGATCTTTATTT

TATAGAATAGACTACACAAAGTCTTTTGGAAAATTAAAATATTTTAACTTCCAACAATTT

TCAGATTTTACTTATAAAAAAATTTAAAATCCTCTACTTTACTCGCATCTTTATTATTTC

TGACTTTCTAGCTACTTAAAGTTAAGGAGGAAATTAACCTCTCTAAGATCGGAAGAGCTC

GTATGCCGTCTTCTGCTTG

Clone 9 (SEQ ID NO: 13)
AATGATACGGCGACCACCGAGATCTACACTCTTTCCCTACACGACGCTCTTCCGATCTCG

CCATAACCACAGCCCAGGCCTCCGTAGCCACAGCACCCATAGCCATGGCCACCATTGTAG

TTTCTGTAGTAGCTGCCACACATGGTGTTGGTTGTTGAGGTCATCCTTGGGTAGGAAGGA

GTGTAGGTGACTTCAGTATGGACACTTCTCCGCAGAGGGCCTTTTATATGCCTCAGTGAA

TCAGAACATAGCGTGCCCCTGCAAAAATATCTCTAAAGGCCTTTCATTGTGCTGAGAAGT

TCTGGCCCTTACGTATCTCTCTGATTTCATATCCTGCTACTCTCCTCCATTTATCTATAA

TGCTCAAACTCTGCTGGCTTTTTGTCTTTTAAAATGCAGCAGGTTTCTTCTCACAATAAG

GAGATCGGAAGAGCTCGTATGCCGTCTTCTGCTTG

Clone 10 (SEQ ID NO: 14)
AATGATACGGCGACCACCGAGATCTACACTCTTTCCCTACACGACGCTCTTCCGATCTAG

AGAGAAGTTATTTAAGACAAGTAAGGTATCAGGTTGTGACTCAAATACCACAGAATCTAG

CTATTGTTAGCAATATTAAGTATATTTTCTTAAATGAAGGATTCTCCATTTACCATATGC

CCCTTGGATAATTTCCAGAGAATTTAATTTTTTAAAAGGAATTTTCACCAATTAAATTAT

TGTTTTGATCAAAAGAGGACCCACTGAACACCTTATTCATTATTAAAATGTATCATAAAA

CTTAATTATGGAGCTGGGTACAGGGGCTCATGCCTGTAATCCCAGCACTTTGGGAGGCTG

AGGCAGGAGGACTGCTTGAGTCCAGGAGTTTGAGACCAGCCTGGGTAACATGGTGAAACC

CTGTCTCTACAAAAAATACAAAAAATTAGCCAGGTGTGGTGAGATCGGAAGAGCTCGTAT

GCCGTCTTCTGCTTG

Clone 11 (SEQ ID NO: 15)
AATGATACGGCGACCACCGAGATCTACACTCTTTCCCTACACGACGCTCTTCCGATCTCC

CAGGGAAGCCAAAAGATTGGACACCCCTCTTTCAAACTATAAATTCCTCCCATAGTTAGT

TTGGCCTATGCTGGGAAATGAACAAGGGTGGCTTTGAGGTTAGAAGCAAAATGGAGTCAG

TTAGGTCAGACTTTTTTTCACTATCATACTTTTTCTATGTCAGATTTATCTCACTTGTAA

TTTTTGCAAGGGTGGTTTCAGAGCCACTAAGCTTGTGGTAATTTTTTACTGCAATAGAAA

ACTAATGCATTAGGTAACCCTCTTTTTTTCCCTCTGATTGCTTGCTCTGGGGTAAGCCAG

CTGCCATGTTGAATTTTTCATTTTGTTACTGAGCAATCAATGGGCTCACTGCCCGACGTG

-continued

CATAGAGGCCAATACTGTGGCACTAGTTTTTGAGAAAAGATCGGAAGAGCTCGTATGCCG

TCTTCTGCTTG

Clone 12 (SEQ ID NO: 16)
AATGATACGGCGACCACCGAGATCTACACTCTTTCCCTACACGACGCTCTTCCGATCTTT

TCAGATTTTATATGTATTAACTCAGAACACACACCTCTTATCACACATATTTTTTCATGT

AATTTATCTAAATCTTATAGAAAAGGGTCCATTTGCATTTTCTCTTATTAGACTCCTGAT

TTCAAATAATATATTACTTATGAGTATTTTTCTGTGCTGTAGTTATTCATTCTTATAGAT

ATGTAACATAATTCCTTTTGCAAAGGTAAAAATTGAGCTATCTCTTGTTGAGGATTTGTT

GATCTCTGTCTAAAGTTTCAAAAATAAAGAACTTTAAAAGCAAAATGTAAATTCCTTTCA

AGTTTTAGTAAAATTACTTCAAACTTAGTAGCTTAAACAATACAGATTTATTATGTTACA

GTTCTGTAAGACAGAAATCTGACTTGATCACACCATGGTAAAACCAAGATACTGCCAGGG

TTGGTTTTTCTTGGGGGGGTCTGTGGGAAGAGTTTGTTTCCTTTGGTTTTCCACAGCC

CAGAGGCTGCTTGCATTCCTTTGATCACTAGATCGGAAGAGCTCGTATGCCGTCTTCTGC

TTG

Clone 13 (SEQ ID NO: 17)
AATGATACGGCGACCACCGAGATCTACACTCTTTCCCTACACGACGCTCTTCCGATCTTA

TTGTTTAGGGAATAATGACAAGGAAAAAAAGTCTGTAGATATTCAGTACAGAGGCACCCA

TCTTTTTAAATTTCTGAAGATTTTTTACTCATGCTTGGTTGAATCCACAGATGCAGAACC

CATAGGTTCAGAGGGCCAGCTGTGCTTTGAAAATATTAGCTTGTGTTTTTATTAGAAAGA

AAACTCTGAGGCCAGGCACGGTGGCTCACGCCTGTAATCCCAGCACTTTGGGAGGCTGAG

GTGGGCGGATCACAAGGTGAGGAGATCGAGACCATTCTGGCTAACATGGTGAAACCCTGT

CTCTACTAAAAATACAAAAAAATTAGCCGGGCGTGGTAGTGAGCACCTAGATCGGAAGAG

CTCGTATGCCGTCTTCTGCTTG

Clone 14 (SEQ ID NO: 18)
AATGATACGGCGACCACCGAGATCTACACTCTTTCCCTACACGACGCTCTTCCGATCTGC

AATTGGTAAAACAGTAAGCAATGAAACAGACACTTCTCAAATATTCCAAGATGGTACACG

CTTTTCAGTGTGTATGATCCAATAAAGCCATTGGAAGTAGGCTTTAATAGTCAAAAAGA

CTATTCAGTTAGATAGGAACTATTTGCCTATAACTATTGGCCAAAAATAGGTTAAAAAAT

TGTTTTAAATTTGTGCTTTACAAAACATGTGGACTTTTTTAGAAAATGTGTCAAATTTCA

AAAGAAATATAGACATTATGGAAAGGTCAGTTAAGCACAGCCCTAATCCTGAAAACATAA

CTATGAAAGATACTAGCTGTTACTTGTAACCAAAAGGAAAAAAAAGATATTAGTAACCAA

TAATTAGCAAACAATGCCCATATATTTCCTTTTTTTTTTTTTTTGAGACAGGGGCT

TACTCAGGCTGGATGTGATCATGAGATCGGAAGAGCTCGTATGCCGTCTTCTGCTTG

Clone 15 (SEQ ID NO: 19)
AATGATACGGCGACCACCGAGATCTACACTCTTTCCCTACACGACGCTCTTCCGATCTTT

AGAAGCTCTATTATACTGGAAAAGAGATATGAGACCCTTCCTACTTTAAGAATCAATGAA

GCCGGGTGTGGTGGCTCACGCCTGTACTCCCAGCATTTTGAGAGGCCAAGCTGGGCAGAT

CACCTGAGGTCGGGAGTTTGAGACCAGCCTAGCCAACATGATGAAATCCTGTTTCTACTA

ATAACACAAAAATTAGCCGGGTGTGGTGGCGCACATCTGGAATCCCAGCTACTCCAGAGG

CTGAGGCAGGAAAATTGCTTGAAGCTGGGAAGCAGAAGTTGCAGTGAAGATCGGAAGAGC

TCGTATGCCGTCTTCTGCTTG

-continued

Clone 16 (SEQ ID NO: 20)
AATGATACGGCGACCACCGAGATCTACACTCTTTCCCTACACGACGCTCTTCCGATCTGG

CTGGACTGAATAGGATAGCCTTAGCTGTAAAATTGGGCTGATCTTTCAAATGGACTCATG

CTTGCCGAATGACTCACGCTCCTGTTTACAAATCAGCTCTGTGAAGAAATGCAGAGTGGG

AGGCTCTGCTTGCCAGACGGAGACCTTAGACCTCCAGGGGCGGAGAACGGAGTACTTCCT

CTGGTGCTCGGCTTCCCTTCCTGGGGGCAGATCTCTCAGCTTCTGGTTGGTGGCTCTCAA

AATCCAGACACAAGGTCAGCTGCAGCCAGCGTGGGCCCTGGAGTAGCTCCAGTTATGGGG

CAGCAATGGCCCCCTCTCATTTTGAGAGCTCACTTTGCCTGTGGATGGTTTTAATCCATC

TGGATAAACTTGAGGCCCATGGGAATACCATATACTATGGTAACCATGTACACTGCTCTA

AAGATGTGGCTGCTGTTGTATAACTTTTTCCTTTATTTTTGTCAATTTCCTATTTTCCAG

AGTCTTGCATACCCACTATGTCTACTGTGATAGTGAACGTAAAAACATACAAGATGTTGG

TGTTATCCTCAATCTCAGATCGGAAGAGCTCGTATGCCGTCTTCTGCTTG

Clone 17 (SEQ ID NO: 21)
AATGATACGGCGACCACCGAGATCTACACTCTTTCCCTACACGACGCTCTTCCGATCTCT

GTGAGAAATCAATGTCTGCTGTTTATAAGCCGCCGGGCTGTGATATCCTGTGAGAGTGGC

CCCAGTGGATGAAGACAGATGCTCTCAAGGAGCGCAGATGACGCGGGTTCCGAAGGACTC

GGCACCCAGCCCGGAGGCCGGCAACATGGGCAAGGGGCCTCTCACGGCTGACCTGTTTCC

TCATCAGCACATCAGGACAATAAGAGCTCCCACTTCACAGGTGGTGAAGAGCCAACGTGG

TGAAGAATGAATAAAGCAGCTCGTGGAAAGTGCTGTGCATGAGGCCTGGCAACCGGTCCC

TGCTCTGAGGTCACCTGCCACGGAGCTGCTGACAGGACCATTAAAAACACAATTGTGCAA

GTGCTCACCCACATTCACAGCAGCAGAATCTCCACCAGCCAAGCATTGGAGACGATCCTT

GCATCCATAGACATGAACAGATGAGCAAAACGTGGTCTATACGGACGATGAAATAGCACT

CAGCCCTAAGAAGAAATAAAATCCCGACAGAGAGATCGGAAGAGCTCGTATGCCGTCTTC

TGCTT

Clone 18 (SEQ ID NO: 22)
AATGATACGGCGACCACCGAGATCTACACTCTTTCCCTACACGACGCTCTTCCGATCTGC

TGAGAGGAGAGGAGAGGCTGGCAGGGGGCTGATGCAGGAGGTGATAGGGCTCCCGGTGAT

AAGAGGTGAGAAGAACAGTCTCTGTGTGCCTAGAGAAGAGATTACCAGAAGTCTGCTATC

TGTTTGTTCGCGGATGTCGGACAGGCAGGATCGGTGATGGCAGGTCTTGGGGGAAGGATT

ATCAGGAGCTAAAAGCTGTCTTCACCTTGGCTGCTAAGAACTCATCTCGGATCTTCTTAG

AATTCCAAATCGGACTTTTCTCCTAGCAGTGGCTACATCCTTAACCTCAAAAATACCCGT

ATTAGCAGATCTACCTCCATGAAATAGACAATTCTTGACAAACTAAGATCGGAAGAGCTC

GTATGCCGTCTTCTGCTTG

Clone 19 (SEQ ID NO: 23)
AATGATACGGCGACCACCGAGATCTACACTCTTTCCCTACACGACGCTCTTCCGATCTGT

TATTTTTCATACTGATGATTCTAGGGCGGTTCCCTGGACTTGGCTGGGACCAGAACTGTC

TCACAGCTGCCAGCGCTCCCCACCCCCATGAGAACCATCGTGCTGAAGATGAAGAGCCAA

AGCCAAACTGACCAGCCTCTGCAACCCCAAGCATCACCGTGTGAGGACAGCGTGATGTGG

AGCCGCGGAGACCCCACGCAGTGCTGCGAGGGGCAACCACATGCAGGGGGGCAGAGGTGT

GGGGGAGCAAGCAGATGCCACCGGCATGCCTAGGAGCCACAGGGAGCATGCGGGCTGGGC

AGTGATGGGAATGAACGTGAACTCCAGTCCTGCCCCAAGAAGTCCTCCGGCCCCTCCTTC

TCAATTCAGGGCACAAAGTGGTAACTGCAGCATGCAGAGGAGTCGAGGAGTCTTCCCTCG

-continued

```
TCCCAGGAGCAGCACCTCGGGCACAGTCTCGGTCCCACAGAACAGCCAAGTGTGGGTTGG

TGGTCTAGAGACCTCCGAAGATCCAGTGGGGGAAGGATGGGCAGCAGAGGGTCTACTCTC

TGAAAATAAGGGGAAGGGATTTTCCCTCCCCACTGCCAAGGTCCCAGCTACTGGACGTGG

GTGGAGATCGGAAGAGCTCGTATGCCGTCTTCTGCCTT
```

These results confirm that the library preparation method produces a library of "sequenceable" DNA templates containing a mixture of fragments of different sequence. The insert DNA from each of the 19 clones sequenced was found to align to a human genome reference sequence (alignment not shown), illustrating that the method produces a library of templates which truly reflect the sequence composition of the starting target fragments (i.e. the clones contain human genomic fragments rather than "junk" sequence).

The invention claimed is:

1. A library of different target nucleic acids comprising a plurality of different polynucleotide duplexes having polynucleotide adapters at each end;
   wherein polynucleotide adapters are forked adapters formed by annealing of partially complementary first and second polynucleotide strands;
   wherein the first polynucleotide strand comprises the sequence set forth in SEQ ID NO: 1; and
   wherein the second polynucleotide strand comprises the sequence set forth in SEQ ID NO: 2.

2. The library of claim 1, wherein a sequence of at least 10 consecutive nucleotides at the 5' end of the first strand of the forked adapters and a sequence of at least 10 consecutive nucleotides at the 3' end of the second strand of the forked adapters are not complementary such that an unmatched region of at least 10 consecutive nucleotides on each strand remains in single stranded form when the double-stranded region is annealed.

3. The library of claim 1, wherein the library of different template polynucleotide molecules comprises sequences of a whole complex polynucleotide sample.

4. The library of claim 3, wherein the different target polynucleotide duplexes are fragments of genomic DNA.

* * * * *